(12) United States Patent
De La Fuente et al.

(10) Patent No.: US 7,781,646 B2
(45) Date of Patent: *Aug. 24, 2010

(54) SPECIFIC GENETIC MODIFICATION OF THE ACTIVITY OF TREHALOSE-6-PHOSPHATE SYNTHASE AND EXPRESSION IN A HOMOLOGOUS OR HETEROLOGOUS ENVIRONMENT

(75) Inventors: Gabriel Iturriaga De La Fuente, Morelos (MX); Johan M. Thevelein, Heverlee (BE); Patrick Van Dijck, Zichem (BE); José Oscar Mascorro-Gallardo, Morelos (MX); Christophe Van Vaeck, Kessel-Lo (BE)

(73) Assignee: Vlaams Interuniversitair Instituut voor Biotechnologie v.z.w., Ghent (BE)

( * ) Notice: Subject to any disclaimer, the term of this patent is extended or adjusted under 35 U.S.C. 154(b) by 791 days.

This patent is subject to a terminal disclaimer.

(21) Appl. No.: 11/065,184

(22) Filed: Feb. 24, 2005

(65) Prior Publication Data
US 2005/0283852 A1 Dec. 22, 2005

(51) Int. Cl.
C12N 15/82 (2006.01)
C12N 15/63 (2006.01)
C12N 15/00 (2006.01)
A01H 5/00 (2006.01)

(52) U.S. Cl. .................. 800/290; 800/287; 800/289; 800/295; 800/278; 435/320.1; 435/468; 536/23.1; 536/23.2; 536/23.6

(58) Field of Classification Search .............. None
See application file for complete search history.

(56) References Cited

U.S. PATENT DOCUMENTS 6,130,368 A * 10/2000 Londesborough et al. ... 800/298
6,833,490 B1 * 12/2004 Goddijn et al. ............. 800/284

FOREIGN PATENT DOCUMENTS

WO  WO 93/17093     * 9/1993
WO  WO 97/42326 A2 * 11/1997

OTHER PUBLICATIONS

Vogel et al The Plant Journal 1998, 13:673-683.*
Romero et al Planta, 1997 201:293-297.*

* cited by examiner

Primary Examiner—Anne Marie Grunberg
Assistant Examiner—Brent Page
(74) Attorney, Agent, or Firm—The Webb Law Firm

(57) ABSTRACT

A method for the preparation of a eukaryotic organism, for example selected from plants, animals and fungi, showing constitutive, inducible and/or organ specific expression of a specifically modified TPS gene, which comprises the steps of providing a TPS gene; designing a suitable modification to the TPS gene by aligning the gene with the corresponding gene of yeast and establishing which part of the gene extends beyond the 5' terminus of the yeast gene; deleting or inactivating a part of the N-terminal region of the TPS gene extending beyond the 5' terminus of the yeast gene, in order to achieve an increased trehalose-6-phosphate synthase activity; cloning the thus modified gene into an expression vector under the control of a constitutive, inducible and/or organ-specific promoter; transforming a plant cell or tissue with the thus obtained expression vector; and regenerating a complete plant from the transformed plant cell or tissue.

16 Claims, 26 Drawing Sheets

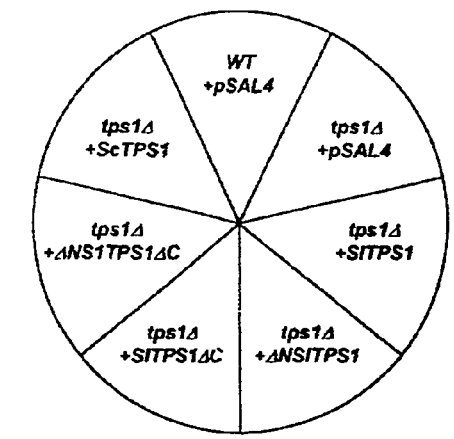
SGal(-ura)
SGlc(-ura)
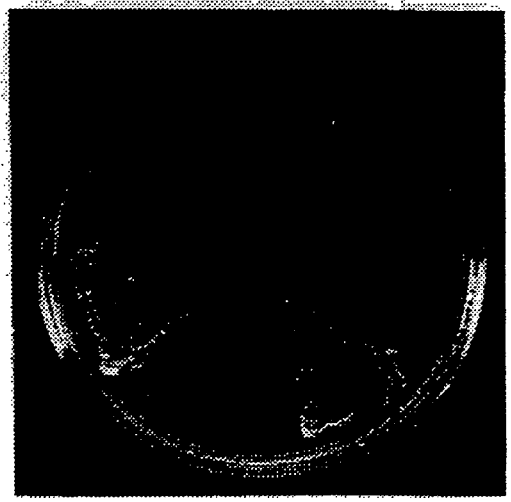
SGlc(-ura)
+100 µM CuSO4
FIG. 6A

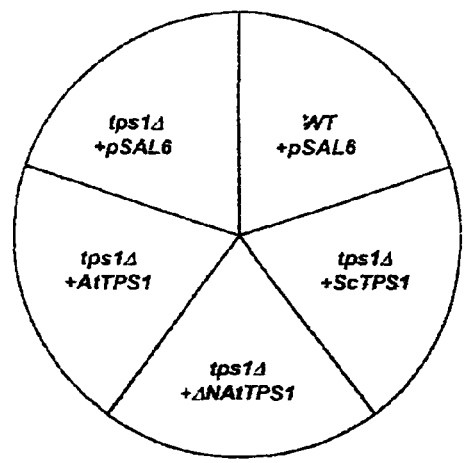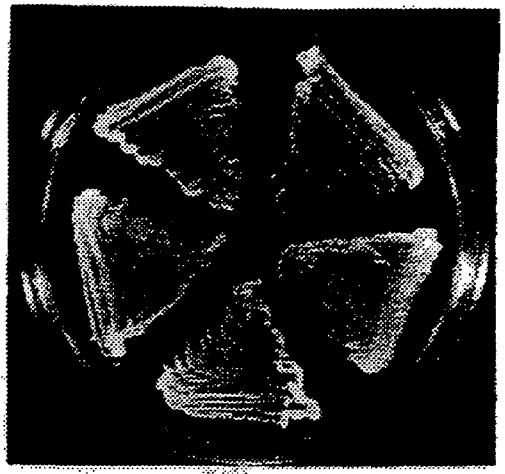
SGal(-his)

SGlc(-his)
SGlc(-his)
+100 µM CuSO₄
FIG. 6B

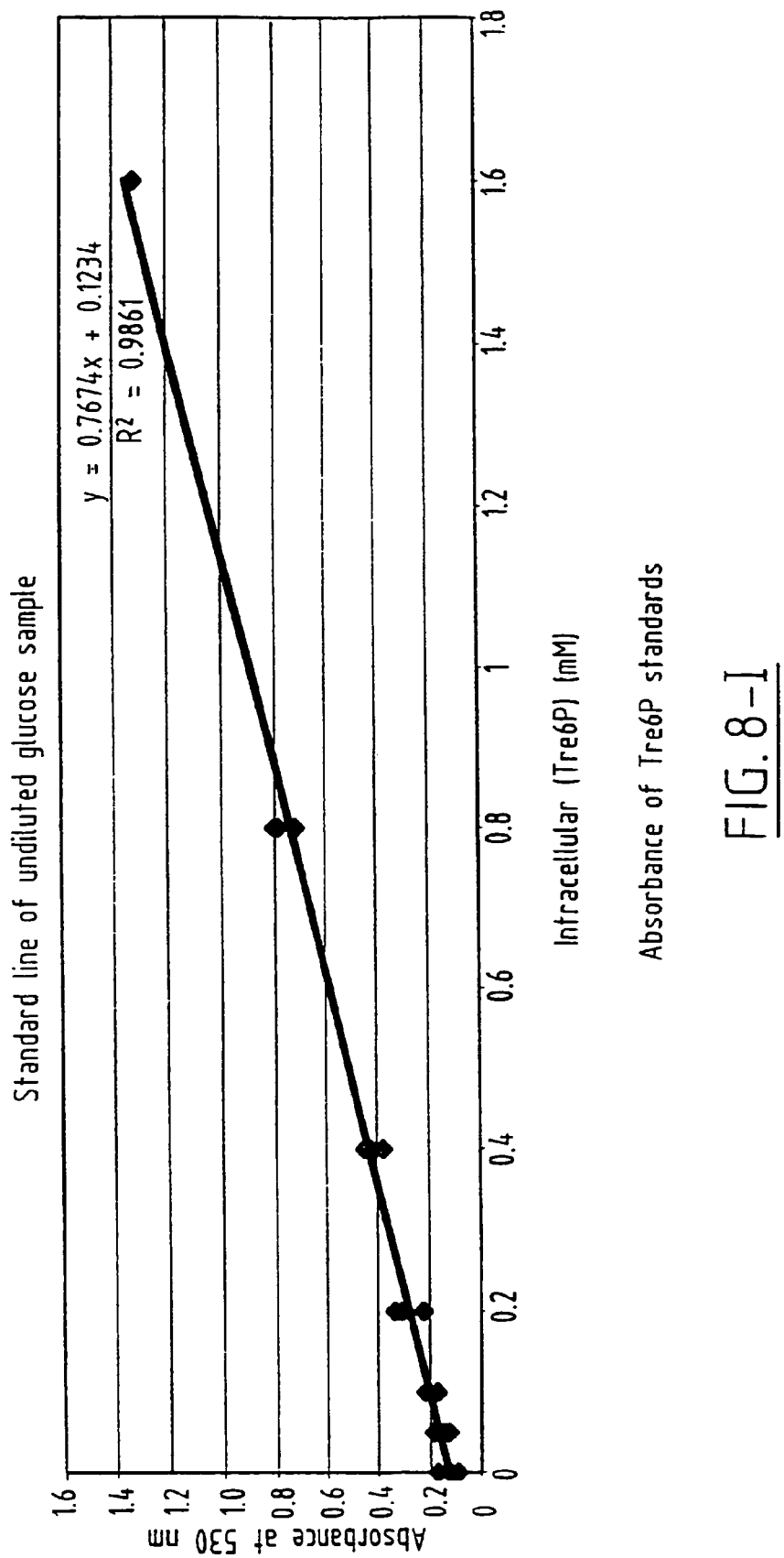
FIG. 8-I

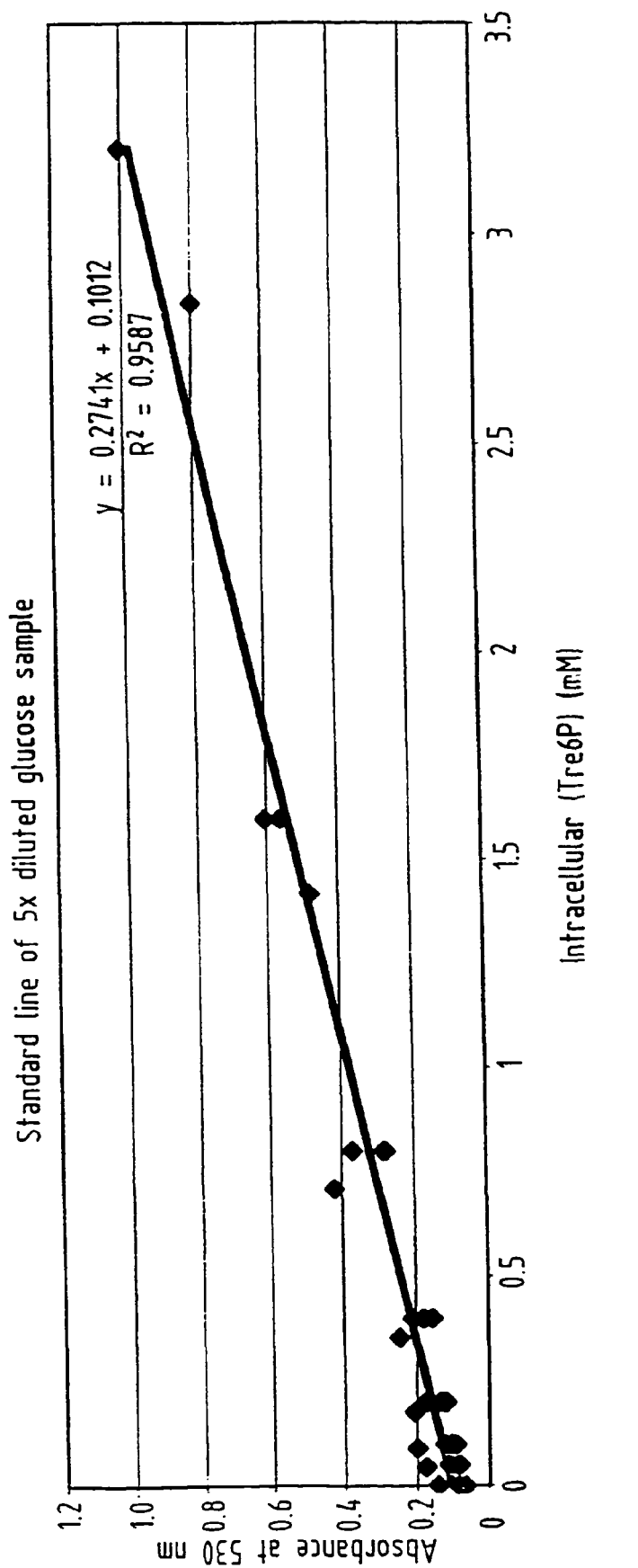
FIG. 8-II

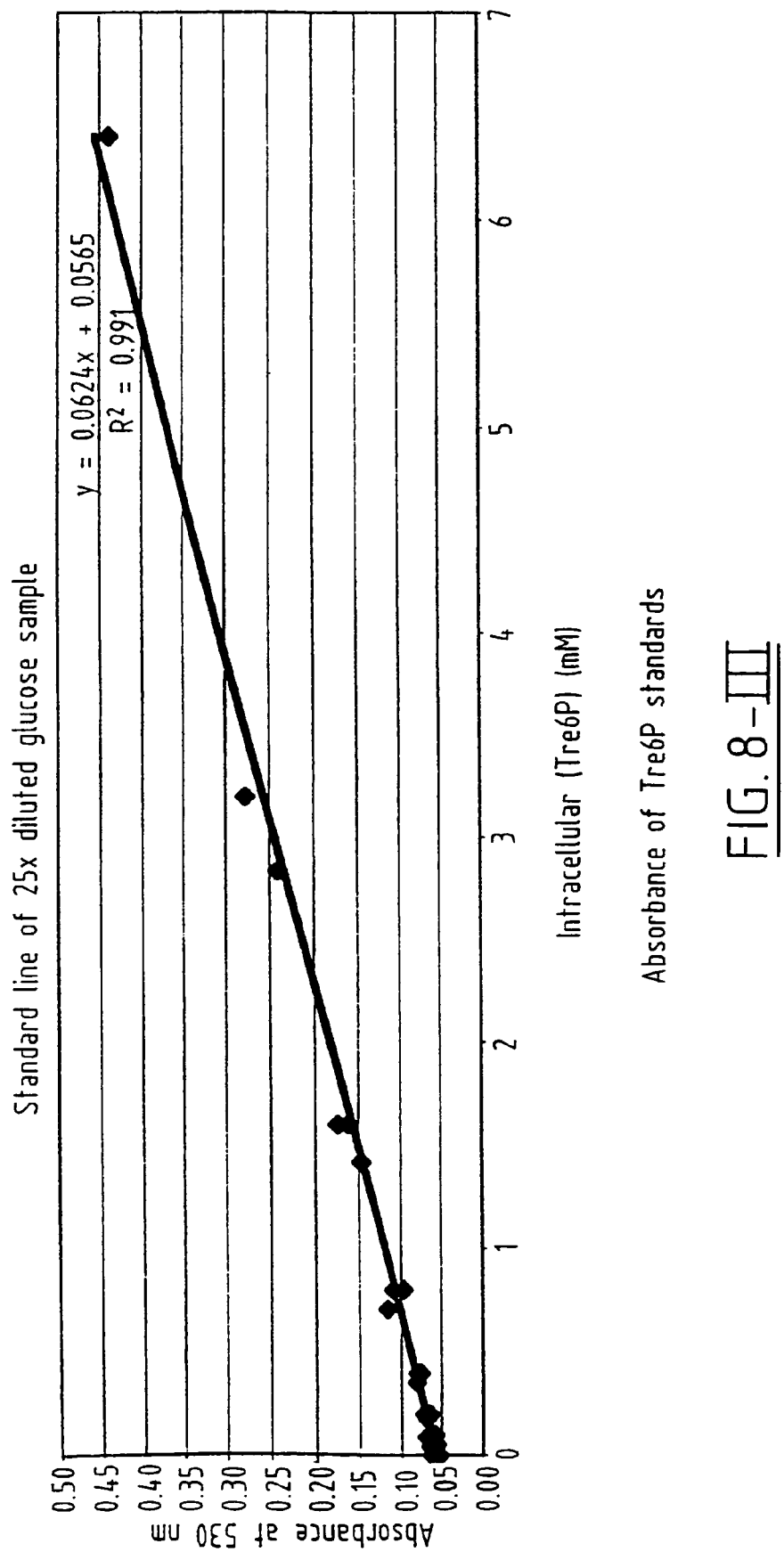
FIG. 8-III

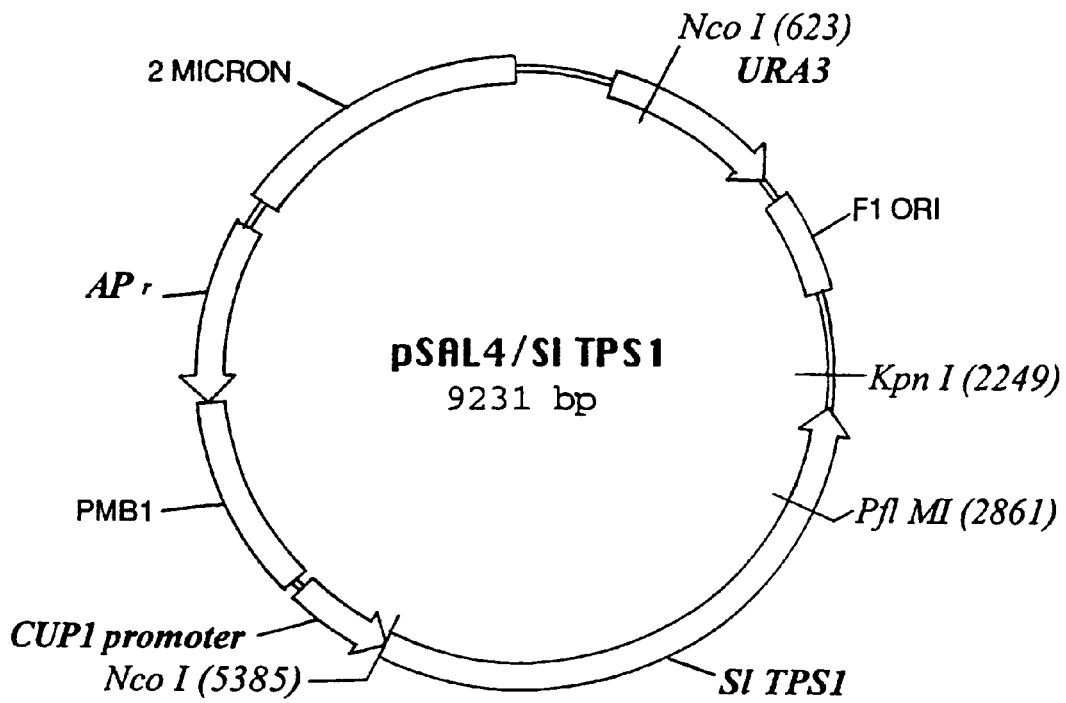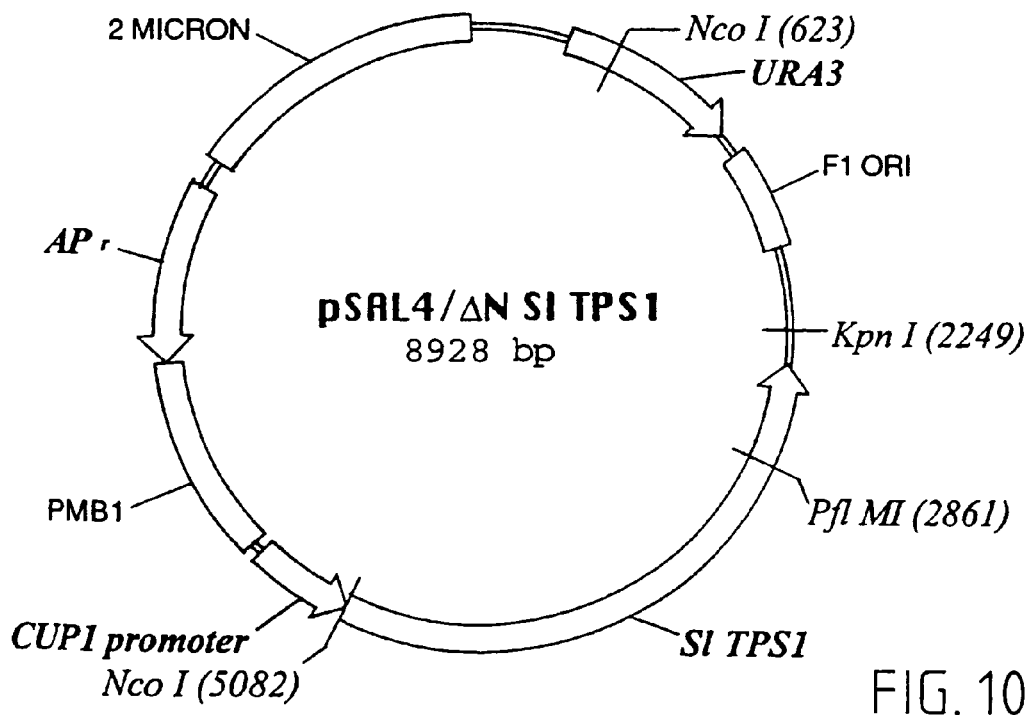
FIG. 10

Chimaeric fusions of TPS and TPP proteins
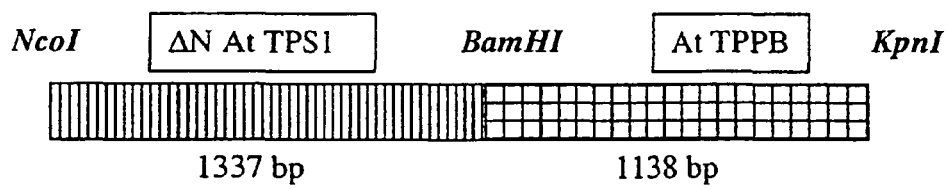
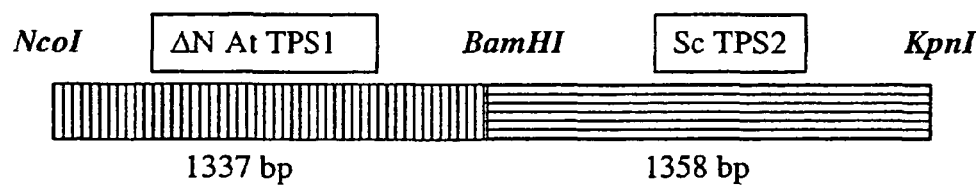
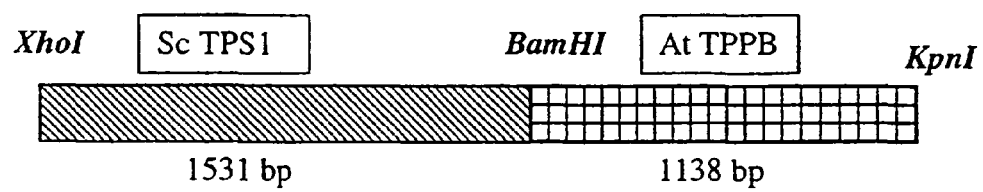
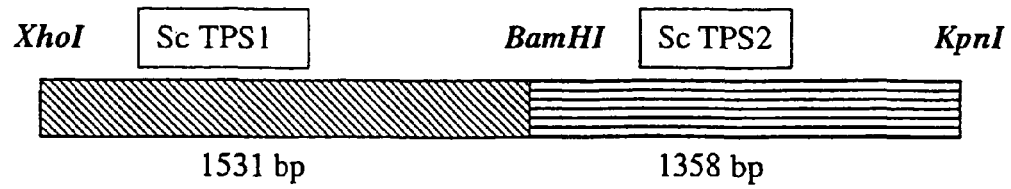
FIG. 13

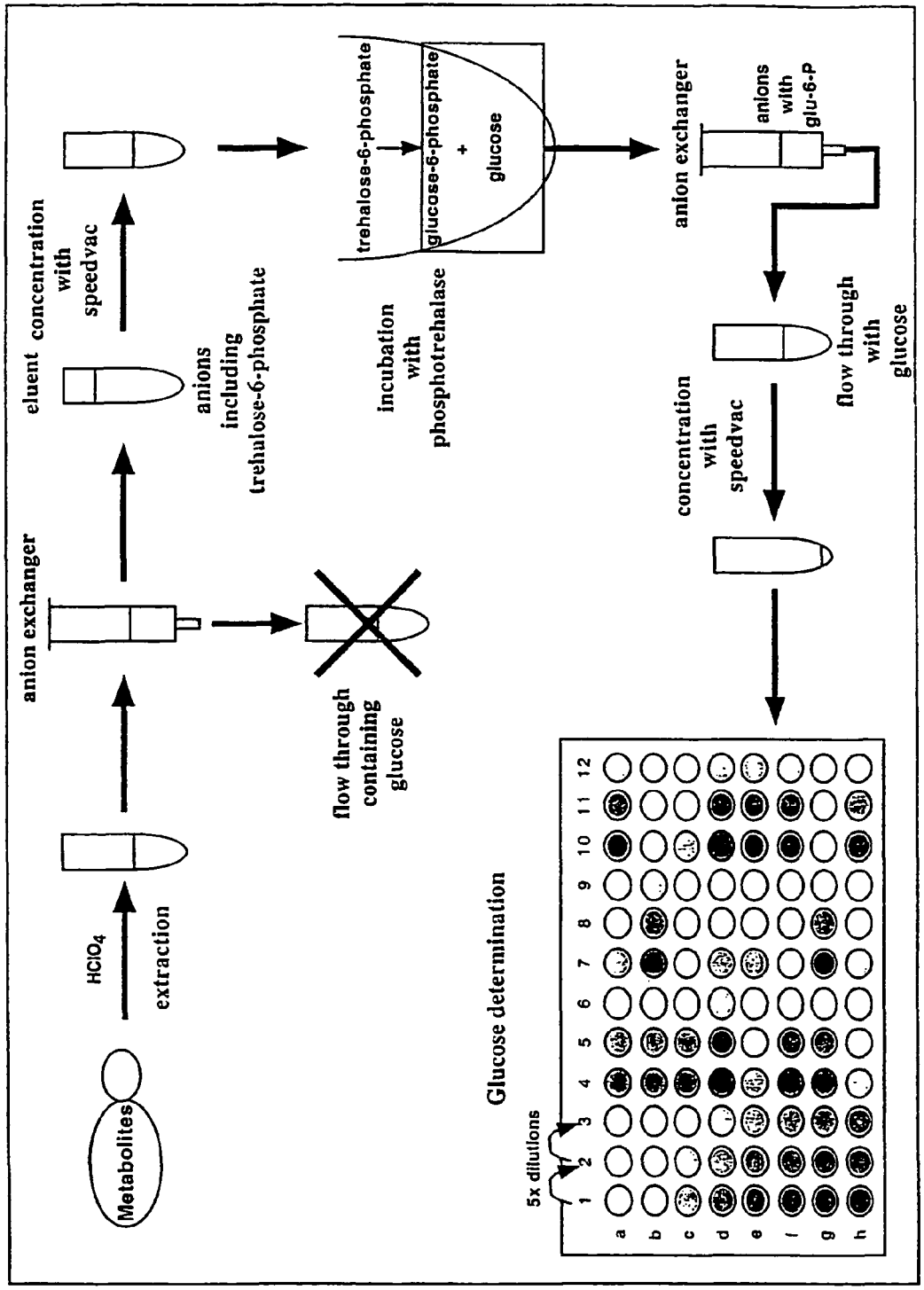
FIG. 16 Overview of the trehalose-6-phosphate assay.

Comparison of specific phosphotrehalase activity in the strains EcVV1 and EcVV3.

SEQUENCE LISTING

<160> NUMBER OF SEQ ID NOS: 21

<210> SEQ ID NO 1
<211> LENGTH: 28
<212> TYPE: DNA
<213> ORGANISM: Artificial sequence
<220> FEATURE:
<223> OTHER INFORMATION: SLTPS-S1 Primer
<220> FEATURE:
<221> NAME/KEY: promoter
<222> LOCATION: (7)...(9)
<223> OTHER INFORMATION: Initiation codon
<220> FEATURE:
<221> NAME/KEY: misc_feature
<222> LOCATION: (5)...(10)
<223> OTHER INFORMATION: NcoI site

<400> SEQUENCE: 1
catgccatgg ctatgcctca gccttacc                                    28

<210> SEQ ID NO 2
<211> LENGTH: 16
<212> TYPE: DNA
<213> ORGANISM: Artificial sequence
<220> FEATURE:
<223> OTHER INFORMATION: Universal primer

<400> SEQUENCE: 2
gtaaacgacg gccagt                                                 16

<210> SEQ ID NO 3
<211> LENGTH: 28
<212> TYPE: DNA
<213> ORGANISM: Artificial sequence
<220> FEATURE:
<223> OTHER INFORMATION: Oligo 5' SLTPS-100
<220> FEATURE:
<221> NAME/KEY: promoter
<222> LOCATION: (7)...(9)
<223> OTHER INFORMATION: Initiation codon
<220> FEATURE:
<221> NAME/KEY: misc_feature
<222> LOCATION: (5)...(10)
<223> OTHER INFORMATION: NcoI site

<400> SEQUENCE: 3
catgccatgg gtcgaggcca gcggttgc                                    28

<210> SEQ ID NO 4
<211> LENGTH: 36
<212> TYPE: DNA
<213> ORGANISM: Artificial sequence
<220> FEATURE:
<223> OTHER INFORMATION: Oligo Ath/TPS-5'
<220> FEATURE:
<221> NAME/KEY: promoter

```
<222> LOCATION: (7)..(9)
<223> OTHER INFORMATION: Initiation codon
<220> FEATURE:
<221> NAME/KEY: misc_feature
<222> LOCATION: (5)..(10)
<223> OTHER INFORMATION: NcoI site

<400> SEQUENCE: 4
catgccatgg ctatgcctgg aaataagtac aactgc                          36

<210> SEQ ID NO 5
<211> LENGTH: 39
<212> TYPE: DNA
<213> ORGANISM: Artificial sequence
<220> FEATURE:
<223> OTHER INFORMATION: Oligo Ath/TPS-3'
<220> FEATURE:
<221> NAME/KEY: terminator
<222> LOCATION: (17)..(19)
<223> OTHER INFORMATION: Termination codon
<220> FEATURE:
<221> NAME/KEY: misc_feature
<222> LOCATION: (9)..(16)
<223> OTHER INFORMATION: NotI site

<400> SEQUENCE: 5
atagttttgc ggccgcttaa ggtgaggaag tggtgtcag                       39

<210> SEQ ID NO 6
<211> LENGTH: 39
<212> TYPE: DNA
<213> ORGANISM: Artificial sequence
<220> FEATURE:
<223> OTHER INFORMATION: Oligo Ath/TPS-(delta)N5'
<220> FEATURE:
<221> NAME/KEY: promoter
<222> LOCATION: (7)..(9)
<223> OTHER INFORMATION: Initiation codon
<220> FEATURE:
<221> NAME/KEY: misc_feature
<222> LOCATION: (5)..(10)
<223> OTHER INFORMATION: NcoI site

<400> SEQUENCE: 6
catgccatgg cttataatag gcaacgacta cttgtagtg                       39

<210> SEQ ID NO 7
<211> LENGTH: 56
<212> TYPE: DNA
<213> ORGANISM: Artificial sequence
<220> FEATURE:
<223> OTHER INFORMATION: Oligonucleotide NA4

<400> SEQUENCE: 7
ctagagcggc cgccagtgtg agtaatttag ttttggttcg ttttggtgtg agcgtc    56

<210> SEQ ID NO 8
<211> LENGTH: 56
<212> TYPE: DNA
<213> ORGANISM: Artificial sequence
<220> FEATURE:
<223> OTHER INFORMATION: Oligonucleotide NA5

<400> SEQUENCE: 8
catggacgct cacaccaaaa cagaaccaaa actaaattat cacactggcg gccgct    56

<210> SEQ ID NO 9
<211> LENGTH: 25
<212> TYPE: DNA
```

-continued

<213> ORGANISM: Artificial sequence
<220> FEATURE:
<223> OTHER INFORMATION: S1 HA 5' primer

<400> SEQUENCE: 9
cgactacgtc ctttgcatag gacac 25

<210> SEQ ID NO 10
<211> LENGTH: 56
<212> TYPE: DNA
<213> ORGANISM: Artificial sequence
<220> FEATURE:
<223> OTHER INFORMATION: S1 HA 3' primer

<400> SEQUENCE: 10
ctggtacctc atgcgtagtc agcgacatca tacggatact gtaccgctgg agcgag 56

<210> SEQ ID NO 11
<211> LENGTH: 25
<212> TYPE: DNA
<213> ORGANISM: Artificial sequence
<220> FEATURE:
<223> OTHER INFORMATION: At HA 5' primer

<400> SEQUENCE: 11
gacgtccttc accagagaag atctc 25

<210> SEQ ID NO 12
<211> LENGTH: 56
<212> TYPE: DNA
<213> ORGANISM: Artificial sequence
<220> FEATURE:
<223> OTHER INFORMATION: At HA 3' primer

<400> SEQUENCE: 12
ctgcatgctc atgcgtagtc aggcacatca tacggataag gtgaggaagt ggtgtc 56

<210> SEQ ID NO 13
<211> LENGTH: 39
<212> TYPE: DNA
<213> ORGANISM: Artificial sequence
<220> FEATURE:
<223> OTHER INFORMATION: CVV5 primer
<220> FEATURE:
<221> NAME/KEY: misc_feature
<222> LOCATION: (8)...(9)
<223> OTHER INFORMATION: Restriction enzyme splice location
<220> FEATURE:
<221> NAME/KEY: misc_feature
<222> LOCATION: (10)...(11)
<223> OTHER INFORMATION: Restriction enzyme splice location

<400> SEQUENCE: 13
tggtggatta atatgaaaac agaacaaacg ccatggtgg 39

<210> SEQ ID NO 14
<211> LENGTH: 45
<212> TYPE: DNA
<213> ORGANISM: Artificial sequence
<220> FEATURE:
<223> OTHER INFORMATION: CVV6 primer
<220> FEATURE:
<221> NAME/KEY: misc_feature
<222> LOCATION: (14)...(15)
<223> OTHER INFORMATION: Restriction enzyme splice location
<220> FEATURE:
<221> NAME/KEY: misc_feature
<222> LOCATION: (17)...(18)
<223> OTHER INFORMATION: Restriction enzyme splice location

```
<400> SEQUENCE: 14
ttaacagctc ttccgcaaac gataaacaat ggactcatat gggcg                      45

<210> SEQ ID NO 15
<211> LENGTH: 32
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (3)...(8)
<223> OTHER INFORMATION: BamHI site

<400> SEQUENCE: 15
cgggatccag ctgtcatgtt tagggcttgt cc                                    32

<210> SEQ ID NO 16
<211> LENGTH: 27
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (3)...(8)
<223> OTHER INFORMATION: BamHI site

<400> SEQUENCE: 16
cgggatccac taaccagaat gtcatcg                                          27

<210> SEQ ID NO 17
<211> LENGTH: 31
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (3)...(8)
<223> OTHER INFORMATION: KpnI site
<220> FEATURE:
<221> NAME/KEY: terminator
<222> LOCATION: (9)...(11)
<223> OTHER INFORMATION: Stop codon

<400> SEQUENCE: 17
ggggtacctc actcttctcc cactgtcttc c                                     31

<210> SEQ ID NO 18
<211> LENGTH: 27
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (3)...(8)
<223> OTHER INFORMATION: BamHI site

<400> SEQUENCE: 18
cgggatccgc taaatctatt aacatgg                                          27

<210> SEQ ID NO 19
<211> LENGTH: 24
<212> TYPE: DNA
<213> ORGANISM: Artificial sequence
<220> FEATURE:
```

```
-continued

<223> OTHER INFORMATION: Nucleotide used in DNA fusion
<220> FEATURE:
<221> NAME/KEY: misc_feature
<222> LOCATION: (4)...(9)
<223> OTHER INFORMATION: KpnI site

<400> SEQUENCE: 19
cggggtacca tggtgggttg agac                                              24

<210> SEQ ID NO 20
<211> LENGTH: 26
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (4)...(9)
<223> OTHER INFORMATION: XhoI site

<400> SEQUENCE: 20
ccgctcgagg gtactcacat acagac                                            26

<210> SEQ ID NO 21
<211> LENGTH: 31
<212> TYPE: DNA
<213> ORGANISM: Artificial sequence
<220> FEATURE:
<223> OTHER INFORMATION: Nucleotide used in DNA fusion
<220> FEATURE:
<221> NAME/KEY: misc_feature
<222> LOCATION: (3)...(8)
<223> OTHER INFORMATION: BamHI site

<400> SEQUENCE: 21
cgggatccgg tggcagagga gcttgttgag c                                      31
```

SPECIFIC GENETIC MODIFICATION OF THE ACTIVITY OF TREHALOSE-6-PHOSPHATE SYNTHASE AND EXPRESSION IN A HOMOLOGOUS OR HETEROLOGOUS ENVIRONMENT

BACKGROUND OF THE INVENTION

1. Field of the Invention

The present invention relates to a method for obtaining eukaryotic organisms, i.e. plants, animals or fungi, with elevated activity and/or altered regulatory capacity of trehalose-6-phosphate synthase. The invention also relates to specifically modified alleles of the trehalose-6-phosphate synthase genes which display unexpected changes in catalytic activity and/or regulatory capacity, and to the transformed plants, or other eukaryotic organisms containing these constructs. The invention is also related to novel methods to measure the level of trehalose-6-phosphate and the activity of trehalose-6-phosphate synthase.

2. Description of the Related Art

The biosynthesis of trehalose consists of two enzymatic steps catalyzed by trehalose-6-phosphate synthase (TPS), which synthesizes trehalose-6-phosphate, and by trehalose-6-phosphate phosphatase (TPP), which forms trehalose. The genes of the trehalose metabolism have been discovered first in yeast and in bacteria, organisms that were known for a long time to accumulate trehalose. Recently, homologues of these genes have also been found in higher plants and animals in which appreciable levels of trehalose had never been detected. However, up to now it has not been possible to demonstrate enzymatic trehalose-6-phosphate synthase activity of these TPS gene products in any in vitro system. Their expression in heterologous systems also does not result in high trehalose accumulation. No successful usage of these plant or animal TPS genes to improve commercially important properties in homologous or heterologous systems has been reported.

In addition to its classical role in storage sugar accumulation, trehalose metabolism is known to play important roles in stress resistance, control of glucose influx into glycolysis and glucose-induced signalling. As outlined below, these phenotypic properties are of high industrial importance.

An amazing capacity for adaptation to survival under strong or even complete dehydration is present in yeast cells, fungal spores, certain invertebrate species and resurrection plants, which resume their vital functions as soon as they are again in contact with water. These anhydrobiotic organisms also withstand freezing, strong vacuum, high doses of ionizing radiation, high pressure and extreme temperatures without suffering damage and many of them accumulate the non-reducing disaccharide trehalose as a protein and membrane protectant.

The protectant function of trehalose has also been demonstrated in vitro. Addition of trehalose to cells, organelles, enzymes, antibodies and foods preserves them under total dehydration for long periods. It also protects them against a variety of other stress conditions, such as high temperature, high pressure and freezing.

In vascular plants, very few species are known where the presence of trehalose has been demonstrated in a convincing way. However, in the so-called desert resurrection plant *Selaginella lepidophylla* a high trehalose level is present. This plant is able to withstand successfully complete dehydration, as opposed to all other higher plants including crop plants.

Deletion mutants in the TPS gene in bacteria and yeast are unable to synthesize trehalose and they lose osmotolerance, thermotolerance and tolerance to high pressure. This suggests that the TPS gene is involved in various forms of tolerance.

It would be highly desirable to be able to express trehalose-6-phosphate synthase activity in plants, animals, micro-organisms or specific parts thereof in order to render them tolerant to stress. In this way, crop plants could be cultured in regions suffering occasionally or continuously from heat, drought or freezing. Perishable foods from plant or animal origin could be preserved by simple dehydration, enabling storage over a prolonged period of time and transport over long distances.

SUMMARY OF THE INVENTION

The present invention for the first time allows to obtain high trehalose-6-phosphate synthase activity and high accumulation of trehalose in organisms where trehalose is normally not made or not accumulated to appreciable levels, such as most higher plants and animals. Hence, it allows for the first time highly-efficient and controlled use of trehalose accumulation in higher plants and animals to enhance stress resistance.

This is achieved in the invention by means of a method for the preparation of an eukaryotic organism, for example selected from plants, animals and fungi, showing constitutive, inducible and/or organ specific expression of a specifically modified TPS gene, comprising the steps of:

a) providing a TPS gene;

b) designing a suitable modification to the TPS gene by aligning the gene with the corresponding gene of yeast and establishing which part of the gene extends beyond the 5' terminus of the yeast gene;

c) deleting or inactivating a part of the N-terminal region of the TPS gene extending beyond the 5' terminus of the yeast gene, preferably the complete extending part thereof, in order to achieve an increased trehalose-6-phosphate synthase activity of the gene;

d) cloning the thus modified gene into an expression vector under the control of a constitutive, inducible and/or organ-specific promoter;

e) transforming a plant cell or tissue with the thus obtained expression vector; and f) regenerating a complete plant from the transformed plant cell or tissue.

The inactivation of the part of the N-terminal region of the TPS gene extending beyond the 5' terminus of the yeast gene can be accomplished by mutagenesis.

It has been found according to the invention that truncation of various genes originating from plants can increase their functionality when expressed in yeast. An increased accumulation of trehalose and high trehalose-6-phosphate synthase activity in comparison to the untruncated gene was observed. By using a constitutive, inducible or organ-specific promoter the expression can be modified and controlled in different ways. The induction can be tissue specific, for example for fruits, time specific, or induced by changes in the environmental conditions. In the latter category heat induction, drought induction, etc. can be included.

BRIEF DESCRIPTION OF THE DRAWINGS

FIG. 6 is a representation of the growth on glucose and fructose containing medium of Wild Type and tps1Δ strains transformed with a yeast expression vector containing a complete or the truncated *S. lepidophylla* TPS gene;

FIG. 8 is a graph of absorbance of Tre6P standards with respect to concentration;

FIG. 10 is a structural diagram of plasmids containing TPS genes;

FIG. 13 is a diagram of the structures of chimaeric fusions of TPS and TPP proteins;

FIG. 16 is an overview of the trehalose-6-phosphate assay;

DETAILED DESCRIPTION OF THE INVENTION

Figure 1:
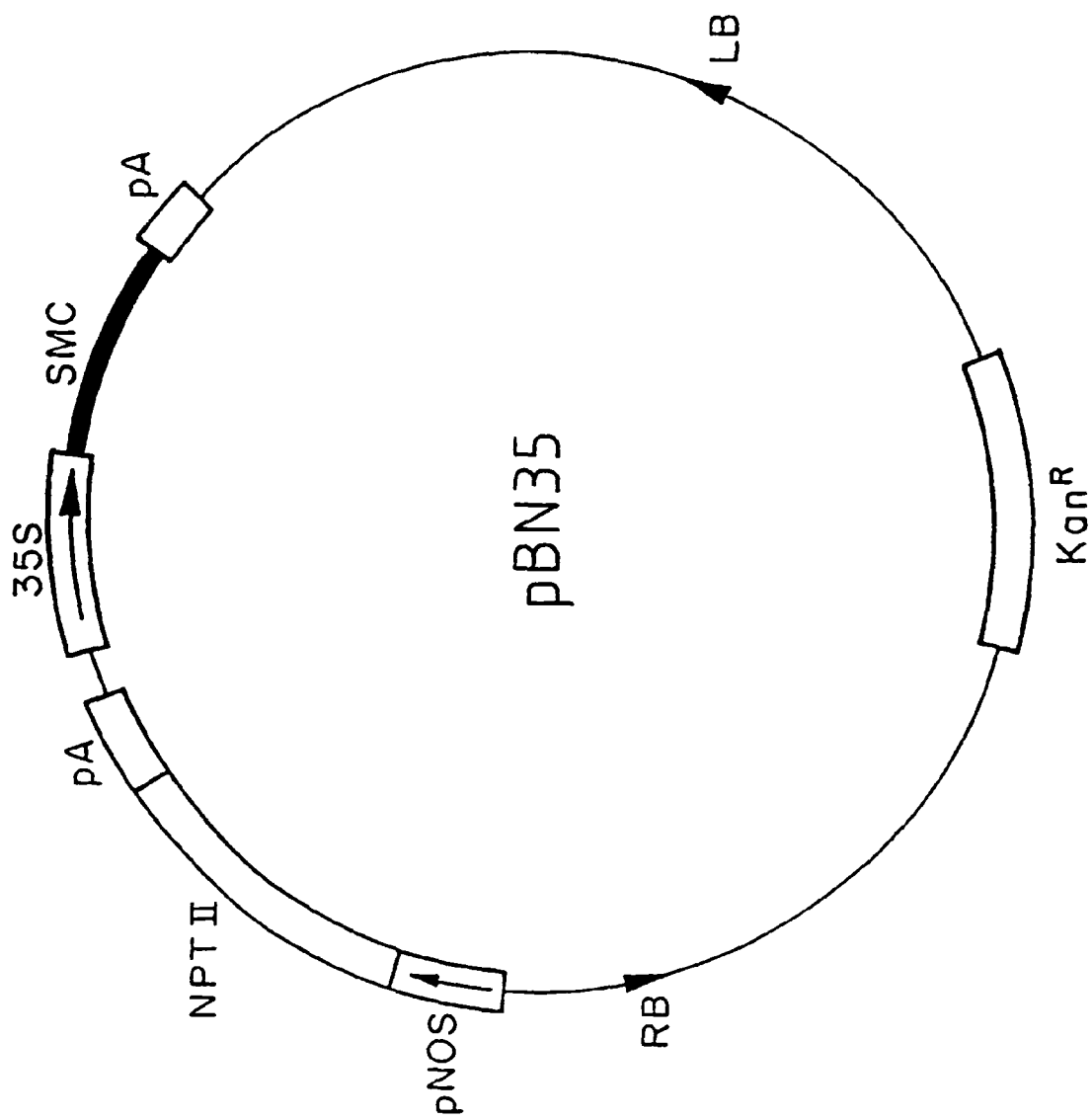
FIG. 1 is a structural diagram of the expression vector pBN35.

The functionality of the modified TPS gene for inferring thermotolerance can be checked in the following test system. Trehalose is required for the acquisition of thermotolerance in yeast. The tps1Δ and tps1Δ tps2Δ yeast deletion mutants are thermosensitive and the phenotype is restored by complementation with the corresponding homologous gene. To determine whether plant or animal TPS is functionally similar to yeast TPS1, tps1Δ and tps1Δ tps2Δ yeast mutants transformed with a plasmid harboring the desired gene are tested for the acquisition of thermotolerance. The ability of the cells to acquire thermotolerance is measured by a lethal heat-shock.

In yeast trehalose metabolism is essential for growth on glucose. Deletion of the TPS gene causes uncontrolled influx of glucose into glycolysis resulting in hyperaccumulation of sugar phosphates and loss of free phosphate and ATP. Trehalose-6-phosphate is known to inhibit hexokinase activity in vitro and the TPS enzyme therefore is thought to exert this control also in vivo by restricting hexokinase activity.

Glucose-induced signalling, and also signalling directly or indirectly induced by related sugars, such as sucrose, plays an important role in many organisms for proper reaction to the availability of external sugar, such as in yeast, or to the internal production of sugar, such as in photosynthetic plants or in the digestive system of animals. In yeast the presence of external glucose, or related sugars, triggers several signalling pathways which causes rapid adaptation of metabolism to the maximal production of ethanol and to rapid growth. In photosynthetic plants sugar-induced signalling controls photosynthetic activity and partitioning of the sugar between the source (photosynthetic parts) and sink organs (non-photosynthetic parts, in particular roots, seeds and fruits). In animals sugar-induced signalling controls the rate of absorption of the sugar from the blood by the storage organs, for instance in mammals it controls the rate of absorption of the blood sugar glucose by the liver.

TPS mutants of yeast are deficient in glucose-induced signalling, a deficiency that is thought to be due to the absence of trehalose-6-phosphate inhibition of hexokinase activity. In higher plants, where trehalose is not accumulated in appreciable amounts, the function of the trehalose metabolism genes is not well understood. Plants in which heterologous TPS or TPP genes have been expressed display altered photosynthetic activity and source-sink partitioning of sugar which indicates possible effects on sugar-induced signalling pathways. This is thought to be due to changes in the trehalose-6-phosphate level caused by the expression of the TPS or TPP genes (Patent application Zeneca-Mogen 6047 PCT).

In the present invention, the unexpected situation is demonstrated that truncation of the N-terminal part of plant TPS genes increases their catalytic activity and therefore likely their regulatory capacity. Hence, the present invention allows alteration of sugar-induced signalling in a more efficient way in higher plants and possibly animals. Moreover, it allows to achieve this by homologous genetic modification in principle in whatever plant and animal species, i.e. by the expression of a truncated form of the homologous TPS enzyme.

In the present invention this alteration in sugar-induced signalling is achieved by the same steps as described hereinabove for the improvement of stress resistance.

The functionality of the modified genes for restoration of the control of glucose influx into glycolysis and restoration of glucose-induced signalling can be checked in the following test system. TPS mutants of yeast are not capable of growing on glucose because they are defective in control of glucose influx into glycolysis and glucose-induced signalling. It is shown according to the invention that expression of modified TPS genes in the tps1Δ yeast strain restores growth on glucose, indicating restoration of the appropriate glucose-signalling controls required for growth.

The present invention according to a further aspect thereof provides for a novel method for the measurement of trehalose-6-phosphate and trehalose-6-phosphate synthase. This method is a highly reliable method for the quantitative determination of trehalose-6-phosphate. The level of trehalose-6-phosphate in all organisms where it has been measured up to now is very low, in the range of 100-200 μM. This low concentration makes an accurate quantification by classical methods, for instance by HPLC, difficult and not very reliable. Chromatographic methods are also tedious because the samples can only be measured one at a time. Other research groups have used the inhibition of yeast hexokinase by trehalose-6-phosphate as an indirect way to estimate the concentration of trehalose-6-phosphate present in cell extracts (Blazquez M. A., Lagunas R., Gancedo C. and Gancedo J. M., 1993, FEBS Lett. 329, 51-54). However, in general such assays are easily prone to interference with other compounds present in the cell extract, especially when derived from organisms like plants and animals which contain many compounds not present in yeast.

In the present invention precise, quantitative measurement of the trehalose-6-phosphate level is achieved by a novel enzymatic assay which makes use of the purified phosphotrehalase enzyme, preferably from *Bacillus subtilis*. The method comprises the following steps:

a) extraction of cells to be analyzed with an extraction medium, preferably a strong acid, that destroys all enzymatic activity but does not degrade trehalose-6-phosphate;

b) neutralization of the extract c) centrifugation of the extract;

d) separation of the acidic compounds, including trehalose-6-phosphate, present in the supernatant from alkaline and neutral compounds, preferably by means of an anion exchange column;

e) treatment of the fraction containing the acidic compounds with purified phosphotrehalase from *Bacillus subtilis* to degrade trehalose-6-phosphate quantitatively into glucose-6-phosphate and glucose;

f) separation of the glucose produced in step e) from the glucose-6-phosphate produced and from the remaining sugar phosphates present, preferably by means of a second anion exchange column;

g) determination of the glucose present, preferably by means of a glucose oxidase and peroxidase assay.

The glucose level measured is identical to the level of trehalose-6-phosphate originally present in the cell extract.

The method established for the measurement of trehalose-6-phosphate can be extended to the measurement of trehalose-6-phosphate synthase activity. Up to now there is no method available that allows the measurement of trehalose-6-phosphate synthase activity based directly on the rate of trehalose-6-phosphate formation. Trehalose-6-phosphate synthase catalyzes the synthesis of trehalose-6-phosphate and UDP from the substrates glucose-6-phosphate and UDP-Glucose.

The classical method for determination of trehalose-6-phosphate synthase activity that is universally used measures the formation of the second product of the enzyme, UDP (Hottiger, T., Schmutz, P., and Wiemken, A., 1987, J. Bacteriol. 169: 5518-5522). However, in cell extracts other enzymes, e.g. glycogen synthase, are present that are able to produce UDP. Therefore, this method is prone to interference from other enzymatic reactions. A method that directly measures the formation of trehalose-6-phosphate is much more preferable. In addition, the said method does not allow the continuous measurement of enzyme activity as a function of time, since termination of the reaction is necessary before UDP can be measured.

It is now shown according to the invention that usage of the purified phosphotrehalase enzyme allows to achieve both goals at once. For this purpose a coupled assay has been developed in which trehalose-6-phosphate is directly and continuously converted to glucose by means of purified phosphotrehalase and the glucose produced continuously measured using the glucose oxidase/peroxidase method. In this assay phosphotrehalase, glucose oxidase and peroxidase are present in excess whereas the trehalose-6-phosphate synthase in the cell extract is the limiting factor in the formation of the coloured product.

The present invention further relates to plants and other eukaryotic organisms that show constitutive, inducible and/or organ specific expression of a specifically modified TPS gene, which plants or other eukaryotic organisms are obtainable by means of the method of the invention. The invention further relates to seeds of those plants or vegetatively reproducible structures of those plants, such as cuttings, somatic embryo's, protoplasts, as well as the further generations of progeny derived from those seeds and structures. The invention also relates to the further progeny of the other eukaryotic organisms.

The TPS gene can be derived from various sources, such as plants, in particular *Selaginella lepidophylla*, *Arabidopsis thaliana*, rice, apple, sugar beet, sunflower (*Helianthus annuus*), tobacco (*Nicotiana tabacum*), soybean (*Glycine max*). The various genes can be expressed in homologous and heterologous environments.

The eukaryotic organism to be transformed can thus be a plant, either the plant from which the gene is derived and now so modified that a modification in the activity of the TPS activity is obtained, or a heterologous plant. Especially preferred hosts for the modified gene are crop plants, in particular plants that are not inherently stress resistant, but can be made stress resistant by the method of the invention. As alternative the goal of the modification can be increased photosynthetic productivity and/or improved carbon partitioning in the whole plant or in specific plant parts.

Other eukaryotic organisms to be transformed are fungi and animals or animal cells. Examples of fungi for which an increase in TPS activity may be beneficial are *Asperqillus niger*, *Agaricus bisporus*, *Pichia pastoris*, *Kluyveromyces lactis* and methylotrophic yeasts. An example of a yeast is *Saccharomyces cerevisiae*. Animal cells are for example mammalian and invertebrate cell cultures used for production of proteins and small molecules, invertebrate cells used for baculovirus expression.

The present invention will be further illustrated in the following examples, which are not intended to be limiting.

EXAMPLES

General Materials and Methods

Reagents

Baker or Sigma reagents of analytical grade were used. The restriction and modification enzymes were from Boehringer-Mannheim; The ZAP cDNA synthesis kit, the Uni-ZAP XR vector and the Gigapack II Gold packaging extracts were obtained from Stratagene Cloning Systems (USA). The Sequenase Version 2.0 kit for determining the nucleotide sequence was purchased from the United States Biochemical Corporation (USA).

The resurrection plant *Selaginella lepidophylla* (Hook. & Grev. Spring.) was collected in dehydrated form from the rocky soil of the arid zones of the States of Morelos and Oaxaca in Mexico. It was subsequently cultivated in controlled conditions (24° C. and 16 hours of light with an average of 50% humidity) in Conviron growth chambers or in a greenhouse. The plants were watered every other day with 20 ml of water for 2 L flower pots. In order to treat *S. lepidophylla* to dehydration stress, the complete plant or microphyll fronds were air-dried by placing them on Whatman 3 MM filter paper. From that moment dehydration time was determined.

Strains

The cDNA bank was plated in the *E. coli* strain XL1-Blue MRF' and the strain SOLR was used to excise the pBluescript from the lambda phage, following the instructions given in the "ZAP-cDNA Synthesis Kit" (Strategene Cloning Systems, Calif. USA; catalogue #200400, 200401 and 2004029). The *E. coli* DH5 alpha strain was used to subclone and make constructs. The *A. tumefaciens* LBA4404 strain was used to transform tobacco and the *E. coli* HB101 strain, carrying plasmid pRK2013 (Bevan, M. (1984) Nucl. Acids Res. 22: 8711-8721) was used to transfer plasmid pIBT36 from *E. coli* to *A. tumefasciens* by means of triparental conjugation as previously described (Bevan, M. (1984), supra).

DNA Manipulation

Recombinant DNA techniques such as bacterial transformation, isolation of DNA from plasmid and lambda bacteriophage were carried out according to standard procedures (Sambrook, J., Fritsch, E. F. & Maniatis, T. (1989) Molecular cloning: A laboratory manual. Second Edition. Cold Spring Harbor Laboratory press, New York). The labelling of radioactive fragments was carried out by the "random-printing" technique with oligonucleotides (Feinberg, A. P. & Vogelstein, B. (1983) Anal. Biochem. 132: 6.130.

Constructs

Figure 4:
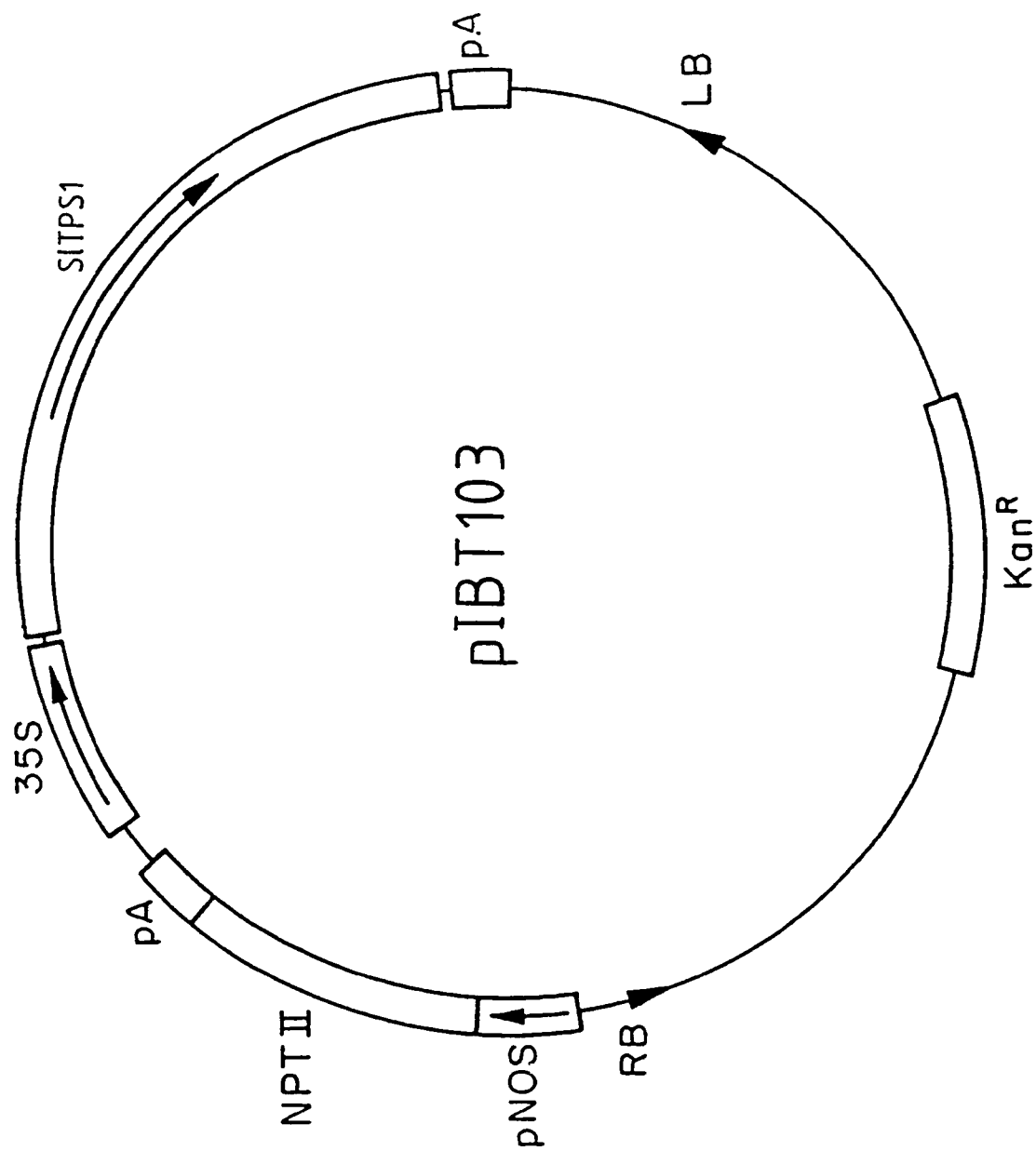
FIG. 4 is a structural diagram of plasmid pIBT103.

The expression vector pBN35 is a derivative of pBin19 (Bevan, M. (1984), supra) that was constructed subcloning the 850 bp of the cauliflower virus CaMV 35S promoter (Guilley, H., Dudley, K., Jonard, G., Richards, K., & Hirth, L. (1982) Cell 21: 285-294) between the HindIII and SalI sites of pBin19 and the 260 bp fragment constituting the polyadenylation signal of the T-DNA nopaline synthetase gene (Bevan, M., Barnes, W. & Chilton, M. D. (1983) Nucl. Acids Res. 11: 369-385) in the SacI and EcoRI sites of the same vector (FIG. 4).

The plasmid pIBT36 (FIG. 5) was constructed by subcloning the sl-tps/p cDNA in the BamHI and KpnI sites of the expression vector pBN35.

Construction of the cDNA Bank of S. lepidophylla

In order to isolate the cDNA clones an expression bank was prepared with mRNA isolated from S. lepidophylla microphylls dehydrated for 2.5 hours, using the ZAP cDNA synthesis kit, the Uni-ZAP XR vector and the Gigapack II gold packaging extracts. The "ZAP-cDNA Synthesis Kit" laboratory manual provided by the manufacturer (Stratagene Cloning Systems, Calif., USA; catalogue #200400, 200401 and 2004029) was followed step by step. PolyA$^+$ RNA was extracted from microphylls of S. lepidophylla, dehydrated for 2.5 hours, in accordance with a known method (Chomczyniski, P. & Sacchi, N. (1987) Anal. Biochem. 162: 156-159). The initial titre of the bank was 2×10$^6$ plaques of bacteriophage/ml and after amplification 1.5×10$^6$ plaques of bacteriophage/ml.

The plasmid pBluescript SK (−) was excised from the bacteriophage by means of the "zapping" technique in accordance with the laboratory manual "ZAP-cDNA Synthesis Kit" (Stratagene Cloning Systems, Calif., USA; catalogue #200400, 200401 and 2004029).

DNA Sequencing

Nested deletions of the insert were created with enzymes ExoIII and Nuclease S1 from the selected clone (Henikoff, S. (1984) Gene 28: 351-359), in order to subsequently determine its nucleotide sequence using the chain termination method with dideoxynucleotides (Sanger, F., Nicklen, S. & Coulson, A. R. (1977) Proc. Natl. Acad. Sci. USA 74: 5463-5467). The DNA sequence was analyzed using the University of Wisconsin Genetics Computer Group (UWGCG) software package (Devereux, J. Haeberli, P. & Smithies, O. (1984) Nucl. Acids Res. 12: 387-395). Hydrophobicity plots were obtained using a known program (Kyte, J. & Doolittle, R. (1982) J. Mol. Biol. 157: 105-132) and protein sequence alignments with the BESTFIT program included in the UWGCG package.

Hybridization of the Nucleic Acids

In order to screen the bank, the bacteriophage plaques were transferred to a Hybond N$^+$ nylon membrane (Amersham Life Sciences) which was treated in accordance with the conventional method for denaturing DNA (Sambrook, J. et al., supra). Second Edition. Cold Spring Harbor Laboratory Press, New York]. The filter was hybridized with oligonucleotides, labelled with the $^{32}$P isotope by means of polynucleotide kinase, using 6×SSC (1×SSC=0.15 M NaCl and 0.015 M sodium citrate) at 37° C. The filter was washed three times, 10 minutes each washing at the same temperature and under the following conditions: 6×SSC; 4×SSC; and 2×SSC.

Southern and Northern gel blot techniques were performed according to standard protocols (Sambrook, J. et al. supra) with the following modifications. For the genomic Southern, the DNA was fractionated on an 0.8% agarose gel in TBE buffer and transferred to a Hybond N$^+$ nylon membrane (Amersham Life Sciences). The filter was hybridized using sl-tps/p cDNA labelled with $^{32}$P isotope as probe, using 2×SSC (1×SSC=0.15M NaCl and 0.015 M sodium citrate) at 65° C. The filter was washed three times, twenty minutes each washing at the same temperature, and under the following conditions: 2×SSC; 1×SSC; and 0.5×SSC. For the Northern, 1.2% agarose gel was used in a MOPS-formaldehyde buffer and a Hybond N$^+$ nylon membrane was also used for the transfer. Hybridization conditions were in 50% formamide and 2×SSC at 42° C. The three successive washings of the filter were performed with 2×SSC, 2×SSC and 1×SSC, respectively at 55° C.

Transformation of Tobacco

The transformation of tobacco (Nicotania tabacum var. SR1) was carried out by means of the leaf disk method (Horsch, R. B., Fry, J. E., Hoffmann, N. L., Eichholtz, D., Rogers, S. G., Fraley, R. T. (1985) Science 227: 1229-1231), using Agrobacterium tumefasciens LBA4404 containing the plasmid pIBT36. The leaf disks were cultivated in Petri dishes containing MS medium with vitamins (Murashige, T. & Skoog, F. (1962) Physiol. Plant. 15: 473-497), hormones (0.1 ppm NAA an 1 ppm BAP) and antibiotics (100 µg/ml kanamycin and 200 µg/ml carbenicillin) to regenerate shoots in 4 to 6 weeks. Shoots were transferred to Magenta pots containing Ms medium with antibiotics (100 µg/ml kanamycin and 200 µg/ml carbenicillin) and without hormones nor vitamins, in order to regenerate roots in 2 to 3 weeks later. The regenerated plants were transferred to pots with soil and cultivated in growth chambers (at 24° C. with 16 hours of light) in order to obtain fertile plants within 4 to 6 weeks.

Trehalose Determination

Trehalose was determined by the degradative method with trehalase (Araujo, P. S.:, Panek, A. C., Ferreira, R. & Panek, A. D. (1989) Anal. Biochem. 176: 432-436). In order to obtain soluble sugars, 500 mg of fresh tissue or 50 mg of dry tissue (frozen in liquid nitrogen) were ground in 0.5 ml of 100 mM PBS buffer, pH 7.0, in a homogenizer for microcentrifuge tubes. Four volumes of absolute ethanol were added and the samples boiled for 10 minutes in tubes with screwcap in order to avoid evaporation. Subsequently, they were centrifuged in microcentrifuge tubes for 2 minutes at 13,000 rpm and the supernatant was recovered. Samples were reextracted again with the same volume of 80% ethanol and the pellet was vacuum dried. The samples were resuspended in 0.250 ml 50 mM PBS, pH 6.5.

For the determination of trehalose, 4 µl (c.a. 15 mU) of trehalase were added (Sigma cat. no. T-8778) to 10 to 30 µl of the extract, and it was incubated for 2 hours at 30° C. As a negative control, a tube with an extract but without trehalase was used nd as a positive control a tube with pure trehalose (Sigma no. cat. T-3663). The volume was brought to 0.5 ml with 50 mM PBS, pH 7.0 and 0.5 µl of glucose oxidase and peroxidase from Sigma kit, cat. no. 510-A, were added in order to determine glucose. Incubation was for 40 min. at 37° C. and the optical density at 425 nm was immediately determined. In order to calculate the glucose concentration, a standard glucose curve was used with values between 0 and 75 mM. The values of the tubes without trehalase were subtracted from those treated with this enzyme in order to calculate the amount of trehalose, taking into account that 1 mol of glucose is ½ mol of trehalose.

Determination of the Enzymatic Activity

To determine the activity of trehalose-6-phosphate synthase, a reported method was followed (Londesborough, J. & Vuorio. 0 (1991) J. Gen. Microbiol. 137: 323-330) that essentially consists of a coupled assay measuring the molar extinction of NADH at 340 nm. The reaction was carried out in a volume of 100 μl containing 40 mM HEPES/KOH pH 6.8 buffer, 10 mM glucose-6-phosphate, 5 mM UDP-glucose 10 mM $MGCl_2$ and 1 mg/ml of bovine serum albumin. The reaction was incubated for 10 min. at 30° C. and was stopped by boiling for 2 min. After cooling the tube, 900 μl containing 40 mM HEPES/KOH pH 6.8 buffer, 10 mM $MgCl_2$, 2.5 μg/ml phosphoenolpyruvate, 0.24 mM NADH, 3.5 units of pyruvate kinase and 5 units of lactate dehydrogenase (Sigma Cat. No. P-0294) were added. The disappearance of NADH at 340 nm, incubating under the same conditions as those mentioned above, was measured spectrophotometrically. In order to determine the specific activity of trehalose-6-phosphose synthase, protein concentration was measured by means of the Bradford method (Bradford, m.m. (1976) Anal. Biochem. 72: 248-254).

Example 1

Selection of TPS Genes

A suitable TPS gene can be selected in various manners. There are two main possibilities to isolate plant TPS genes. First of all, functional complementation of *Saccharomyces cerevisiae* cells that are deleted for the TPS1 gene is a straightforward approach. Deletion of this gene causes a pleiotropic phenotype in yeast (Van Aelst et al., 1993, Mol. Microbiol. 8, 927-943). One of the phenotypes is that such cells cannot grow on glucose. Construction of cDNA libraries from interesting plants in yeast expression plasmids can be used to transform a yeast strain that is deleted for TPS1. Transformants can than be checked for the restoration of growth on glucose. On the other hand, the synthesis of trehalose in the transformants can also be measured. If transformants are found that restore the growth on glucose medium or that produce again trehalose, the plasmid DNA can be isolated and the inserts sequenced. Based on the sequence it can then be concluded whether a real TPS homologue or a suppressor has been isolated.

Secondly, a comparison of the amino acid sequences of trehalose-6-phosphate synthase, deduced from the reported nucleotide sequences, can be made. The sequences used come from *E. coli*, EC-otsA [Kaasen, I., McDougall, J., Strom, A. R. (1994) Gene 145: 9-15]; *Schizosaccharomyces pombe*, SP-TPS1 [Blazquez, M. A., Stucka, R., Feldman, H & Gancedo, C. (1994) J. Bacteriol. 176: 3895-3902]; Aspergillus niger, AN-TPS1 [Wolschek, M. F. & Kubicek, C. P. (1994) NCBI: Seq. ID 551471; unpublished]; *Saccharomyces cerevisiae*, SC-TPS1 (McDougall, J., Kaasen, Y. & Strom, A. R. (1993) FEMS Microbiol. Let. 107: 25-301; *Kluyveromyces lactis*, KL-GGS1 [Luyten, K., de Koning W., Tesseur, Y., Ruiz, M. C., Ramos, J., Cobbaert, P., Thevelein, J. M., Hohmann, S. (1993) Eur. J. Biochem. 217: 701-713].

As an example for the isolation of a plant homologue the isolation of the cDNA of S1-TPS will be described here.

Dehydrated resurrection plants, *Selaginella lepidophylla*, were collected from rocky soil in arid zones of the States of Morelos and Oaxaca in Mexico. They were subsequently cultivated in 2 L flower pots at 24° C. with 16 hours of light and 50% average humidity in Conviron growth chambers. The plants were watered every other day with 20 ml of water.

In order to isolate the cDNA clones, an expression bank was prepared using 5 Φg of mRNA isolated from 50 g of *S. lepidophylla* microphylls dehydrated for 2.5 hours. After synthesizing the cDNA, it was cloned using 1 Φg of Uni-ZAP XR vector. The bacteriophages were packaged in vitro and were subsequently screened with a mixture of degenerated oligonucleotides that code for consensus regions in trehalose-6-phosphate synthase of the reported sequences of *E. coli* and yeast. One of the isolated clones corresponds to a cDNA (sl-tps) with a complete coding region.

Analysis of the deduced amino acid sequence resulted in 53% identity for trehalose-6-phosphate synthase and 298 for trehalose-6-phosphate phosphatase, as compared with reported sequences of trehalose-6-phosphate synthase of bacteria and various yeasts.

Homology of the protein encoded by sl-tps, called SL-TPS, to trehalose-6-phosphate synthase, maps at the N-terminal region of the former and the homology of SL-TPS to trehalose-6-phosphate phosphatase can be found throughout the whole sequence.

The isolation procedure as described for *S. lepidophylla* can be used for any other plant, preferably monocots and dicots. This method is of general application because the degenerate oligos that were used to fish *Selaginella* TPS were tested successfully in *Arabidopsis thaliana*. Using a PCR reaction a fragment of the *A. thaliana* TPS gene could be isolated. Based on this fragment the complete *A. thaliana* TPS gene was isolated.

Example 2

Preparation of Constructs

1. Construction of Yeast Expression Vectors Containing Plant TPS Genes.

A 3.1-kb fragment containing the full length S1TPS1 gene was obtained after amplification by PCR (94° C., 3 min, 1 cycle; 94° C., 1 min, 50° C., 1 min, 72° C., 2 min, 40 cycles; 72° C., 10 min, 1 cycle) using Expand High-fidelity DNA polymerase (Boehringer). As oligonucleotides, SLTPS-S1 (5'-CATG<u>CCATGG</u>CTATGCCTCAGCCTTACC-3', (SEQ ID NO: 1) bold indicates initiation codon and underlined NcoI site) and universal (5'-GTAAACGACGGCCAGT-3') (SEQ ID NO: 2) primers were used with S1-TPS1 cDNA cloned in pBluescript SK as template. The PCR-fragment was digested with NcoI and KpnI and cloned in pSAL4. Yeast tps1) and tps1) tps2) mutant strains were transformed and selected on SDGa1 (-ura) plates. Complementation was assayed in SDG1c (-ura minimal medium plus 100 ΦM $CuSO_4$).

For the construction of the N-terminal deletion construct the following oligonucleotides were used:

oligo 5' SLTPS-100 5'-CATG<u>CCATGG</u>GTCGAGGC-CAGCGGTTGC-3' (SEQ ID NO: 3), bold indicates initiation codon and underlined NcoI site.

oligo 3' universal 5'-GTAAACGACGGCCAGT-3' (SEQ ID NO: 2).

A 2.8-kb fragment was obtained after amplification by PCR (94° C., 3 min, 1 cycle; 94° C., 1 min, 50° C., 1 min, 72° C., 2 min, 40 cycles; 72° c., 10 min, 1 cycle) using Expand High-fidelity DNA polymerase (Boehringer) with oligos SLTPS-100 and universal, and S1-TPS1 cDNA cloned in pBluescript SK as template. The PCR-fragment was digested with NcoI and KpnI and cloned in pSAL4. Yeast tps1Δ and tps1Δ tps2Δ mutant strains were transformed and selected in SDGal (-ura). Complementation was assayed in SDGlc (-ura minimal medium plus 100 μM CuSO$_4$).

For the construction of yeast expression vectors containing the *A. thaliana* TPS gene RT-PCR was used.

Total RNA (5 Φg) extracted from *Arabidopsis thaliana* cv. Columbia seedlings grown for 2 weeks in liquid MS medium containing 100 mM NaCl, was reversed transcribed using SuperScript II (GIBCO) using an oligo dT (25 mer) primer. A PCR reaction (94° C., 3 min, 1 cycle; 94° C., 1 min, 50° C., 1 min, 72° C., 2 min, 40 cycles; 72° C., 10 min, 1 cycle) was done using Expand High-fidelity DNA polymerase (Boehringer) to amplify AtTPS1 using oligos Ath/TPS-5' (5'-CATG <u>CCATGG</u>CTATGCCTG-GAAATAAGTACAACTGC-3' (SEQ ID NO: 4); bold indicates initiation codon, underlined is NcoI site) and Ath/TPS-3' (5'-ATAGTTTT <u>GCGGCCGC</u>TTAAGGTGAG-GAAGTGGTGTCAG-3' (SEQ ID NO: 5); bold indicates termination codon, underlined NotI site). A 2.8-kb fragment was obtained corresponding to the expected size, digested with NcoI and NotI, and cloned in pSAL6. Yeast tps1) and tps1) tps2) mutant strains were transformed. Transformants were grown in SDGal (-his minimal medium). Complementation was assayed in SDG1c (-his minimal medium plus 100 ΦM CuSO$_4$).

For the construction of the N-terminal deletion construct the following oligonucleotides were used:

oligo Ath/TPS-)N5'

5'-CATG <u>CCATGG</u>CTTATAATAGGCAACGACTACTTGTAGTG-3' (SEQ ID NO: 6), bold indicates initiation codon and underlined NcoI site.

oligo Ath/TPS-3'

5'-ATAGTTTT <u>GCGGCCGC</u>TTAAGGTGAGGAAGTGGTGTCAG-3' (SEQ ID NO: 5); bold indicates termination codon, underlined NotI site.

Total RNA (5 μg) extracted from *Arabidopsis thaliana* cv. Columbia seedlings grown for 2 weeks in liquid MS medium containing 100 mM NaCl, was reverse transcribed using SuperScript II (GIBCO) and an oligo dT (25 mer) primer. A PCR reaction (94° C., 3 min, 1 cycle; 94° C., 1 min, 50° C., 1 min, 72° C., 2 min, 40 cycles; 72° C., 10 min, 1 cycle) was done using Expand High-fidelity DNA polymerase (Boehringer) to amplify AtTPS1 using oligos Ath/TPS-?N5' and Ath/TPS-3'. A 2.6-kb fragment was obtained corresponding to the expected size, digested with NcoI and NotI, and cloned in pSAL6. Yeast tps1Δ and tps1Δtps2Δ mutant strains were transformed. Transformants were grown in SDGal (-his minimal medium).

Complementation was assayed in SDGlu (-his minimal medium).

2. Construction of Plant Expression Vectors Containing Plant TPS Genes

To clone in plant expression vectors, plant trehalose-6-phosphate synthase genes were first tested in a yeast tps1Δ mutant and subsequently subcloned in appropriate plant transformation vectors. The 2.9-kb AtTPS1 and 2.6-kb ΔNAtTPS1 coding regions were isolated after digestion of plasmids pSAL6::AtTPS1 and pSAL6::ΔNAtTPS1 with NcoI and KpnI enzymes. This latter site is downstream of NotI site in pSAL6.

The 3.1-kb S1TPS1 and 2.8-kb)NS1TPS1 coding regions were isolated after digestion of plasmids pSAL4.S1TPS1 and pSAL4.dNS1TPS1 with NcoI and KpnI enzymes, as well. All DNA fragments were ligated to a 57-bp fragment containing AtTPS1 5'leader, XbaI and NcoI sites. This fragment was obtained after annealing oligonucleotides NA4 (5'-CTA-GAGCGGCCGCCAGTGTGAGTAATT-TAGTTTTGGTTCGTTTTGGTGTGAGCGTC-3') (SEQ ID NO: 7) and NA5 (5'-CATGGACGCTCACACCAAAACA-GAACCAAA-ACTAAATTATCACACTGGCGGCCGCT-3') (SEQ ID NO: 8).

Figure 2:
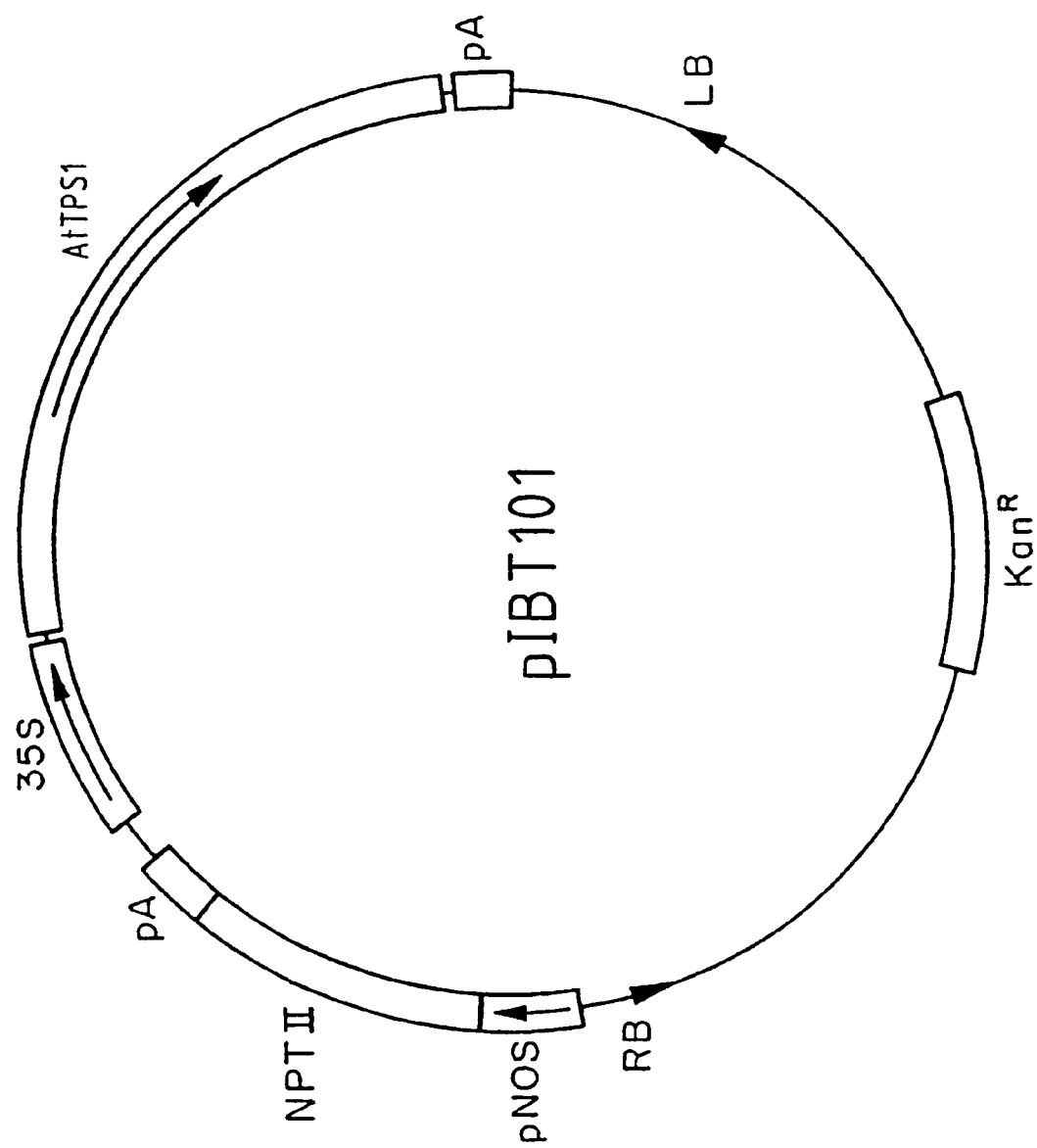
FIG. 2 is a structural diagram of plasmid pIBT101.
Figure 3:
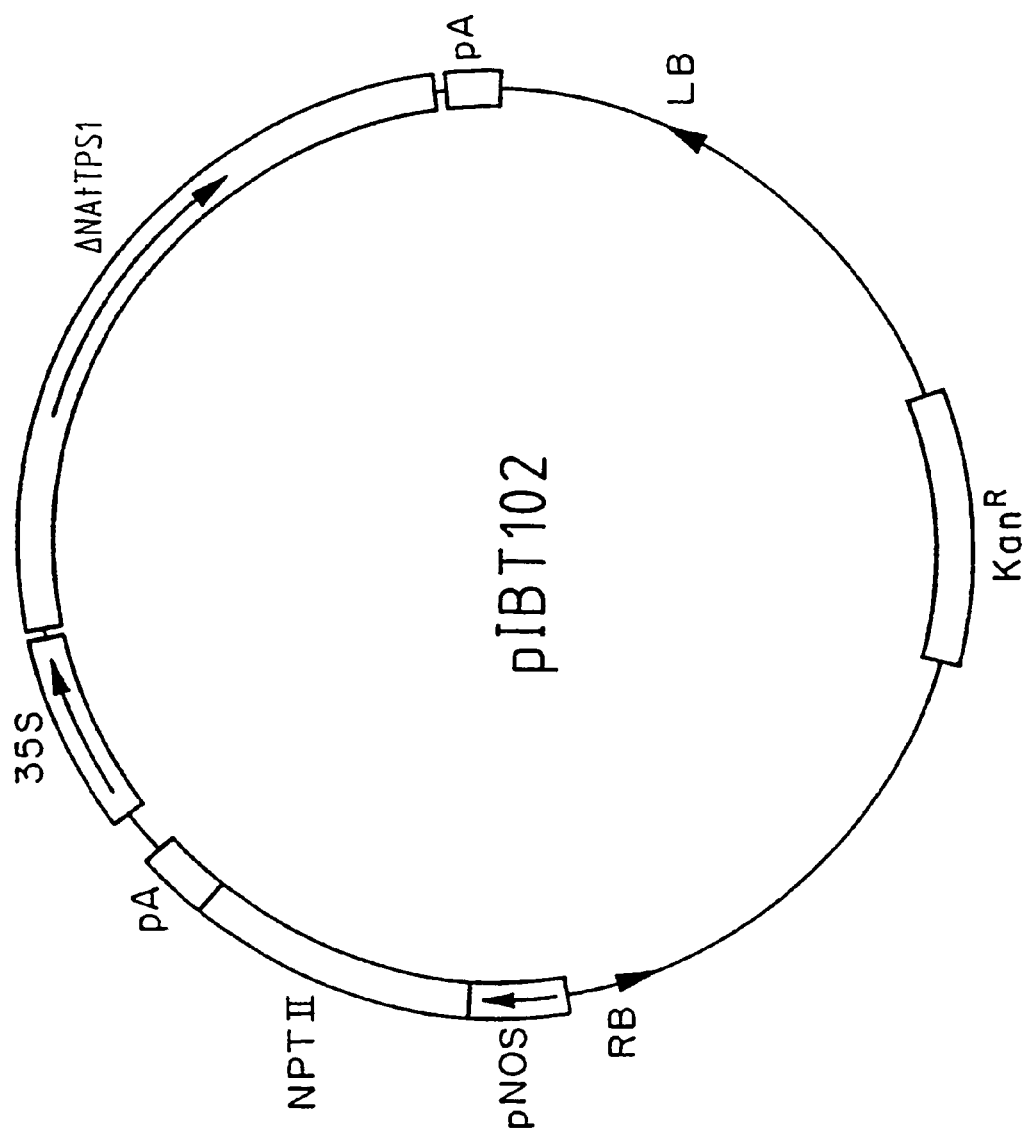
FIG. 3 is a structural diagram of plasmid pIBT102.
Figure 5:
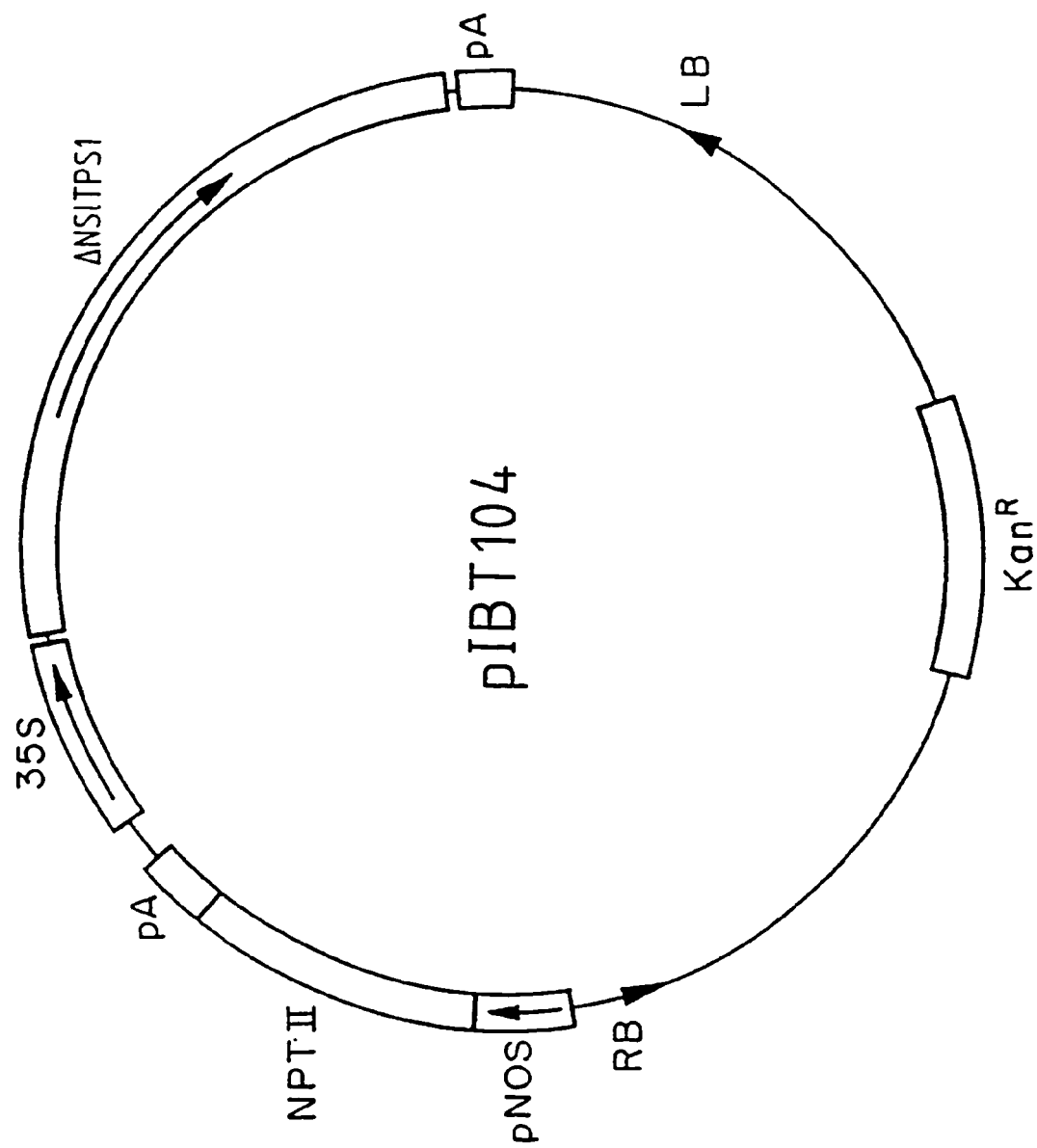
FIG. 5 is a structural diagram of plasmid pIBT104.

Each ligated leader-coding-region cassette was further ligated to the expression vector pBN35 digested with XbaI and KpnI (FIG. 1) leading to plasmids pIBT101 containing AtTPS1 (FIG. 2), pIBT102 containing ΔNAtTPS1 (FIG. 3), pIBT103 containing S1TPS1 (FIG. 4) and pIBT104 containing ΔNS1TPS1 (FIG. 5). The vector pBN35 allows the expression of any gene under the control of the cauliflower virus (CaMV) 35S promoter (Guilley, H., et al., Cell 21: 285-294 (1982)) which is a strong and constitutive promoter.

These plasmids were used to obtain transgenic plants, transformed by means of the *Agrobacterium* system, that when regenerated were capable of producing trehalose. These constructs can be expressed in any plant that can be transformed using the *Agrobacterium* system or by any other method known in the state of the art.

The expression vector pBN35 is a derivative of pBin19 (Bevan, M., Nucl. Acids Res. 22: 8711-8721 (1984)) that was constructed by subcloning the 850 bp of the cauliflower virus CaMV 35S promoter (Guilley, H. et al., supra) between the HindIII and SalI sites of pBin19 and the 260 bp fragment constituting the polyadenylation signal of the T-DNA nopaline synthetase gene (Bevan, M. et al., Nucl. Acids Res. 11: 369-385 (1983)) in the SacI and EcoRI sites of the same vector (FIG. 1).

3. Construction of HA-Tagged S1 TPS1, At TPS1, ΔN S1 TPS1 and ΔN At TPS1 Alleles.

Figure 9:
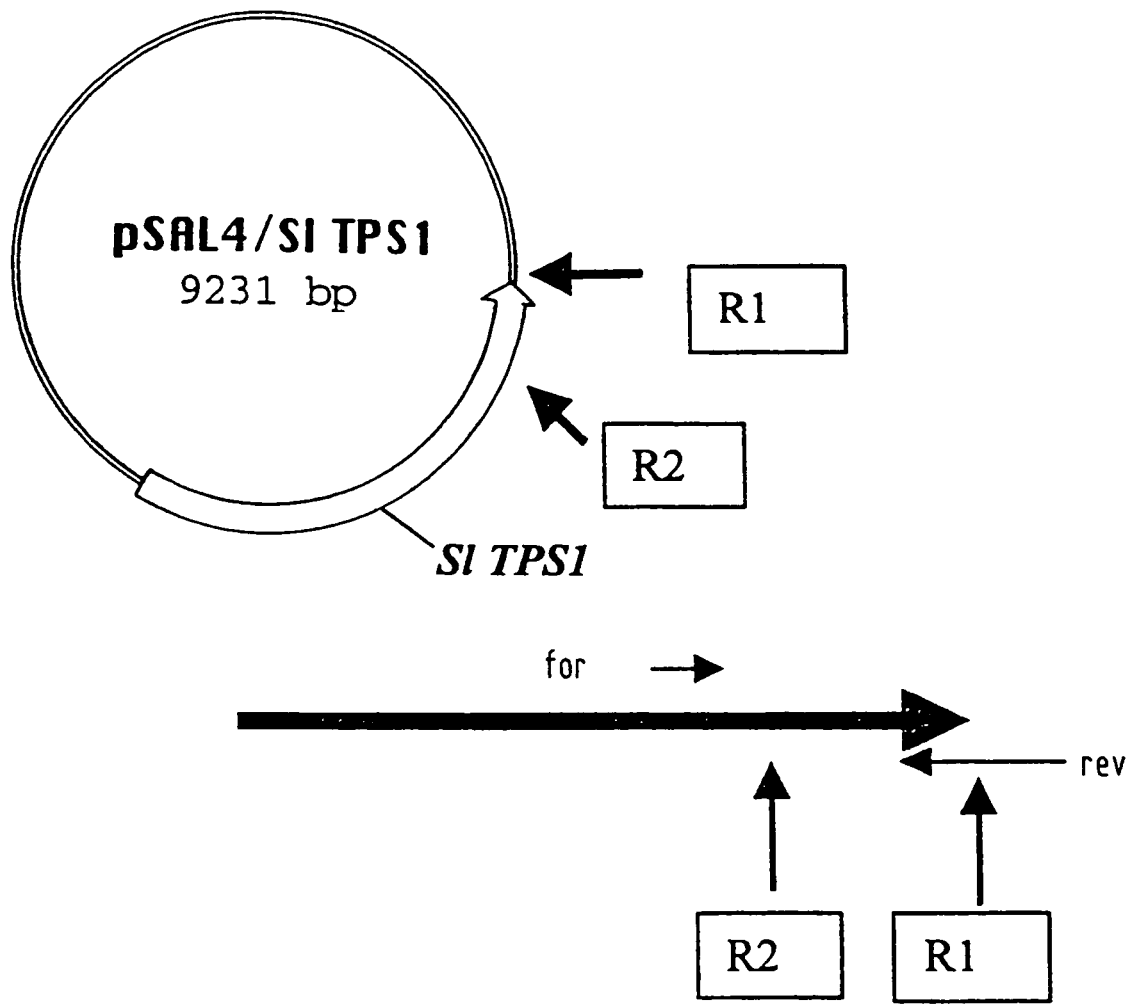
FIG. 9 is a schematic representation of the method used to make tagged versions of TPS genes.

In order to determine whether the difference in activity between the full length plant TPS1 genes and the N-terminally deleted alleles is caused by the fact that the former ones are not able to form a correct TPS complex when expressed in yeast cells, we have made tagged versions of these genes. The scheme as shown in FIG. 9 was used to make these constructs. FIG. 10 shows the resulting plasmids.

The plasmid containing the plant TPS genes is digested with two unique restriction sites, one cutting just after the gene (R1) and the second cutting close to the 3' of the gene (R2). The fragment that is removed by the combined use of R1 and R2 is replaced with a fragment obtained by PCR that is also digested with R1 and R2. The R2 site is located within the PCR product whereas the R1 site is part of the reverse primer (rev). The constitution of the reverse primer is as follows:

5' R1-STOP-HAtag-Codons for 6 amino acids of relevant gene-3'

Table 1 shows the primers that we have used:

The primers can be used for both the full length genes as well as the ΔN alleles.

TABLE 1

| 5' primers | 3' primers |
|---|---|
| S1 HA 5': | S1 HA 3': |
| 5' CGACTACGTCCTTTGCATAG | 5' CT GGT ACC <u>TCA</u> TGC GTA |

TABLE 1-continued

| 5' primers | 3' primers |
|---|---|
| GACAC3'<br>(SEQ ID NO: 9) | GTC AGC GAC ATC ATA CGG ATA<br>CTG TAC CGC TGG AGC GAG 3'<br>(SEQ ID NO: 10) |
| At HA 5':<br>5'GACGTCCTTCACCAGAGAAG<br>ATCTC3'<br>(SEQ ID NO: 11) | At HA 3':<br>5' CT GCA TGC TCA TGC GTA<br>GTC AGG CAC ATC ATA CGG ATA<br>AGG TGA GGA AGT GGT GTC 3'<br>(SEQ ID NO: 12) |

In table 2 the different vectors and restriction enzymes that were used are indicated.

TABLE 2

| | | Restriction enzyme: | |
|---|---|---|---|
| PCR product (template): | Vector: | R1 | R2 |
| Sl (pSal4 vector) | pSal4/Sl TPS1<br>pSal4/ΔN Sl TPS1 | KpnI | PflmI |
| At (pSAL6 vector) | pSal6/At TPS1<br>pSal6/ΔN At TPS1 | SphI | AspI |

Example 3

Functional Complementation of Yeast tps Mutants with Modified Plant TPS Genes

1. Complementation of the Growth Defect of tps1Δ and tps1Δtps2Δ Strains

Tps1Δ and tps1Δtps2Δ strains were transformed with yeast expression vectors containing either full length or N-terminal deleted *S. lepidophylla* or *A. thaliana* TPS genes. As controls, Wild Type, tps1Δ or tps1Δtps2Δ strains were transformed with an empty plasmid, or with a plasmid containing the yeast TPS1 gene. Transformants were tested for growth on glucose and fructose containing medium. FIG. 6 shows the growth on glucose and fructose containing medium of Wild Type and tps1Δ strains transformed with a yeast expression vector containing a complete or the truncated *S. lepidophylla* TPS gene. The lanes are as follows: 1. WT, 2. tps1Δ, 3. tps1Δ+ΔNTPS1 Sl, 4. tps1Δ+TPS1 Sl, 5. tps1Δ+TPS1 Sc, 6. tps1Δtps2Δ, 7. tps1Δtps2Δ+ΔNTPS1 Sl, 8. tps1Δtps2Δ+TPS1 Sl, 9. tps1Δtps2Δ+TPS1 Sc, 10. tps1Δtps2Δ+TPS2Sc.

The full length clone can only complement the tps1Δtps2Δ strain. It cannot complement the growth defect of a tps1Δ strain on glucose or fructose. However, if the N-terminal part is deleted, the *S. lepidophylla* gene expressed from the Cu-inducible promoter can complement the growth defect in a tps1Δ strain. This clearly illustrates the beneficial effect of the N-terminal deletion.

If the plant gene is expressed under the control of a stronger promoter, also the full length clone can complement the tps1Δ strain for growth on glucose or fructose (not shown).

2. Restoration of Trehalose Levels in tps1Δ Strains

Trehalose was measured in yeast cells using the method of Neves et al. (Microbiol. Biotechnol. 10: 17-19 (1994)). In this method, trehalose is degraded by trehalase and the glucose that is formed is measured by the glucose oxidase/peroxidase method. Briefly, cells were collected on a filter, with pores of 0.22 or 0.45 µm, on a vacuum flask and washed with water. Cells were collected, the weight was determined and they were frozen in liquid nitrogen. For extraction of the trehalose, $Na_2CO_3$ (0.25M) was added to the cells (1 ml per 50 mg of cells) and they were boiled for 20 min. After centrifugation, 10 µl of the supernatant was used to measure the trehalose content. Each sample was neutralized by adding 5 µl of a 1M acetic acid solution. To each sample 5 µl of buffer T1 (300 mM NaAc+30 mM $CaCl_2$ pH 5.5) and 20 µl of trehalase solution (isolated from the fungus *Humicola grisea*) were added. The samples were incubated at 40° C. for 45 min. In this step, trehalose is broken down to glucose. In parallel to the samples, trehalose standards and control samples were also measured. After this incubation the tubes were centrifuged briefly and 30 µl of the supernatant was used for glucose determination.

To each sample, 1 ml of glucose oxidase/peroxidase solution containing o-dianisidine (0.1 mg/ml) was added and the mixture was incubated for 1 h at 30° C. The reaction was stopped by the addition of 56% (v/v) sulfuric acid. For each sample the extinction at 546 nm was measured.

The trehalose levels were measured in *S. cerevisiae* tps1Δ strains transformed with plasmids containing the SlTPS1, ΔNSlTPS1, AtTPS1 or ΔNAtTPS1 genes under the control of a Cu-inducible promoter. Table 3 shows the results of three independent experiments. The abbreviation 1Δ stands for tps1Δ.

TABLE 3

| | | trehalose<br>µmol/g ww | TPS activity<br>µkat/g protein |
|---|---|---|---|
| WT + pSAL4 | galactose | 58.4 | 0.63 |
| | glucose | 48.5 | 0.51 |
| | fructose | 72.5 | 0.58 |
| 1 Δ + pSAL4 | galactose | 3.2 | 0.05 |
| | glucose | NG | NG |
| | fructose | NG | NG |
| 1 Δ + pSAL4::SlTPS1 | galactose | 2.1 | 0.01 |
| | glucose | NG | NG |
| | fructose | NG | NG |
| 1 Δ + pSAL4::ΔN SlTPS1 | galactose | 43.5 | 0.41 |
| | glucose | 49.2 | 0.65 |
| | fructose | 89.2 | 0.43 |
| 1 Δ + pSAL6::AtTPS1 | galactose | 1.6 | 0 |
| | glucose | NT | NT |
| | fructose | NT | NT |
| 1 Δ + pSAL6::ΔN AtTPS1 | galactose | 36.5 | 0.1 |
| | glucose | 41.4 | 0.12 |
| | fructose | 59 | 0.07 |
| 1 Δ + pSAL4::ScTPS1 | galactose | 43.4 | 1.25 |
| | glucose | 37.1 | 1.01 |
| | fructose | 54.4 | 1.53 |
| 1 Δ + pSAL4::ΔC SlTPS1 | galactose | 0 | 0 |
| | glucose | NG | NG |
| | fructose | NG | NG |
| 1 Δ + pSAL4::ΔNΔC Sl TPS1 | galactose | 8.2 | 0.08 |
| | glucose | 48.2 | NT |
| | fructose | NT | NT |

The results in this table confirm the results shown in FIG. 6. The full length clones cannot complement the growth defect of a tps1Δ strain on glucose or fructose containing medium. Furthermore on galactose these full length clones are not capable of producing trehalose in tps1Δ strains. However, if the N-terminal part of either the *S. lepidophylla* or the *A. thaliana* TPS gene is deleted and the tps1Δ strains are transformed with plasmids containing these genes, these strains are able to grow on glucose or fructose and these strains also produce high levels of trehalose. ("-" means that no measurement could be made because the cells are unable to grow under this condition; "ND" means not detectable)

3. Deletion of the N-Terminus is Necessary to Obtain TPS Activity in an In Vitro Assay.

Trehalose-6-phosphate synthase activity was measured by a coupled enzyme assay as described by Hottiger et al. (J. Bacteriol., 169: 5518-5522 (1987)). Crude extracts were desalted on a Sephadex G-25 column with a bed volume of 2 ml, pre-equilibrated with 50 mM Tricine buffer pH 7.0. The assay mixture contained 50 mM Tricine/KCl (pH 7.0), 12.5 mM $MgCl_2$, 5 mM UDP-glucose, 10 mM glucose-6-phosphate, enzyme sample and water in a total volume of 240 µl. In controls, glucose-6-phosphate was omitted and replaced by water. The assay mixtures were incubated at 30° C. for 30 min. The reaction was stopped by boiling for 5 min. After cooling, assay mixtures were centrifuged at 13000 rpm for 10 min. The UDP formed in the supernatant was measured enzymatically. The assay mixture contained 66 mM Tricine/KCl (pH 7.6), 1.86M phosphoenolpyruvate, 0.3 mM NADH, 5U lactic dehydrogenase, and 60 µl of sample in a total volume of 990 µl. The reaction was started by addition of 10 µl pyruvate kinase, and incubated at 37° C. for 30 min. The decrease in absorbance at 340 nm was recorded and used to calculate the enzyme activity.

$$\text{enzyme activity}(\mu\text{kat/gprot.}) = \frac{\Delta OD_{340} \times 240\,\mu l \times 10^{12}}{60\,\mu l \times 6.22 \times 10^6 \times 30\,\text{min} \times 60\,\text{s/min} \times 30\,\mu l \times \text{mg/ml protein}}$$

$1\text{kat}=6\times10^7$ units.

The results of the TPS activity measurements are shown in Table 3. They indicate that only the N-terminal deleted TPS genes, and not the full length clones, result in high activity of trehalose-6-phosphate synthase when expressed in yeast.

After construction of the HA-tagged alleles these alleles were introduced in tps1Δ and tps1Δtps2Δ strains. The following strains were obtained:

PVD164: a leu2-3/112 ura3-1 trp1-1 his3-11/15 ade2-1 can1-100 GAL SUC2+tps1Δ::TRP1+pSAL4/Sl TPS1 HAtag (URA3)

PVD165: a leu2-3/112 ura3-1 trp1-1 his3-11/15 ade2-1 can1-100 GAL SUC2+tps1Δ::TRP1+pSAL4/?N Sl TPS1 HAtag (URA3)

PVD179: a leu2-3/112 ura3-1 trp1-1 his3-11/15 ade2-1 can1-100 GAL SUC2+tps1Δ::TRP1 tps2Δ::LEU2+pSAL4/Sl TPS1 HAtag (URA3)

PVD181: a leu2-3/112 ura3-1 trp1-1 his3-11/15 ade2-1 can1-100 GAL SUC2+tps1Δ::TRP1 tps2Δ::LEU2+pSAL4/ΔN Sl TPS1 HAtag (URA3)

The presence of the HA-tag did not interfere with the function of the plant genes. Expression from the CUP1 promoter (pSal vectors) of the full length plant alleles did not restore the growth defect on glucose of a tps1Δ strain. Expression of the N-terminally deleted alleles did restore growth on glucose as we have seen for the non-HA tagged alleles.

The expression of the full length and N-terminally deleted HA-tagged Sl TPS1 genes was tested in both the tps1Δ and the tps1Δtps2Δ strain.

Strains PVD164 (tps1Δ+Sl TPS1-HA), PVD165 (tps1Δ+ΔN Sl TPS1 HA), PVD179 (tps1Δtps2Δ+Sl TPS1-HA) and PVD181 (tps1Δtps2Δ+ΔN Sl TPS1-HA) have been grown till stationary phase in SDgal-URA (+$CuSO_4$). The cells were washed in extraction buffer (for 1 liter: 10.7 g $Na_2HPO_4.2H_2O$, 5.5 g $NaH_2PO_4.H_2O$, 0.75 g KCl, 246 mg $MgSO_4.7H_2O$, 1 mM PMSF, pH 7.0) and resuspended in 500 µl extraction buffer. Extracts were made by vortexing 2 times for 1 min in the presence of glass beads. The extracts were cleared by centrifugation for 20 min.

10 µg of the extracts were run on a 7.5% PAGE gel. After blotting, the nitrocellulose membranes were incubated for 1 h in TBST containing 2% BSA (5×TBS: 6 g Tris+45 g NaCl, pH 7.4; TBST=1×TBS+0.05% Tween20). The filters were then incubated for 1 h with anti-HA antibodies (anti-HA high affinity, rat monoclonal antibody clone 3F10, Boehringer Mannheim) diluted 1:1000 in TBST containing 2% BSA. The filters were washed 3×5 min in TBST and subsequently incubated for 45 min with the secondary antibody (Sigma A-6066; anti-rat) diluted 1:20000 in TBST containing 2% BSA. The filters were then washed 3×5 min in TBST. Afterwards, the filters were washed for 5 min in TBS. The alkaline phosphatase developing mixture (10 ml 100 mM Tris, pH 9.5; 50 mM $MgCl_2$; 100 mM NaCl, 37.5 µl X-phosphate and 50 µl nitro blue tetrazolium (NBT)) was added to the filters and when the bands became visible the reaction was stopped by adding $H_2O$. The results are presented in FIG. 11.

The calculated molecular weight of the full length Sl Tps1 protein (without the HA tag) is 109353 whereas the ΔN Sl Tps1 protein has a molecular weight of 99453.

In order to find out wether the difference in complementation capacity between the full length TPS1 gene and the N-terminally deleted TPS1 gene is caused by the fact that the full length protein can not make a correct TPS complex FPLC analysis of yeast extracts prepared from tps1Δ strains transformed with either the full length Sl TPS1 or the ΔN Sl TPS1 gene was performed. The extracts were separated on a gelfiltration column (Superdex 200 HR 10/30) and fractions of 750 µl were collected as described by Bell et al., (J. Biol. Chem., 373, 33311-33319, 1998). The first fraction that contains proteins is fraction 10. Based on the column characteristics and based on calibration experiments the proteins in fraction 10-14 correspond to very large protein complexes ranging from 800 000 to 400 000 daltons.

Figure 11:
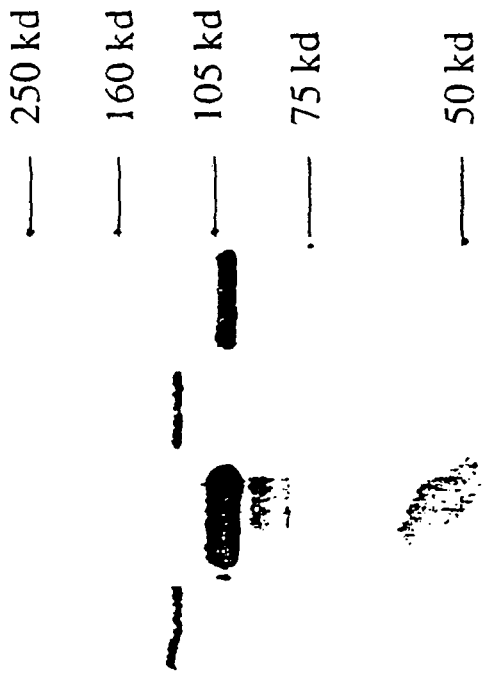
FIG. 11 is an illustration of western blot results using anti-HA antibodies.
Figure 12:
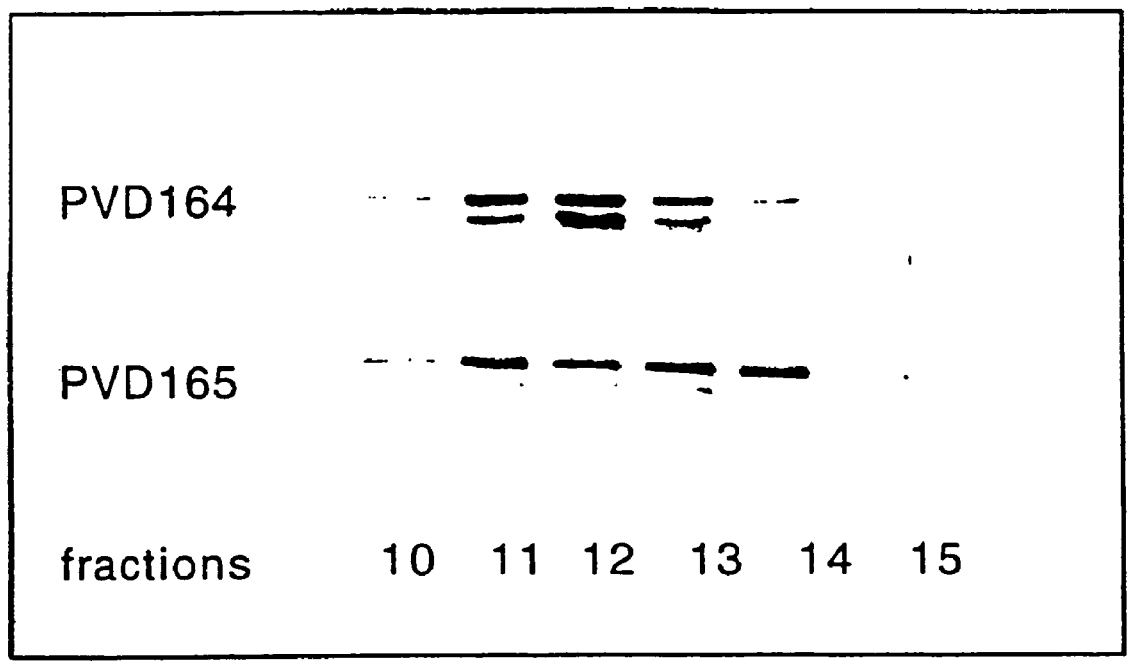
FIG. 12 is an illustration of results for PVD164 and PVD165.

FIG. 11 gives the result of the western blot using anti-HA antibodies. Here we only show fractions 10 to 15. The free TPS1 protein is present in fractions 25-27 (not shown). Very important is the fact that both the full length and the ΔN Sl TPS1 alleles are able to form complexes with the other subunits of the TPS complex. This might indicate that the N-terminal region itself may exert an inhibitory function directly on the remainder of the plant Tps1 protein.

The fact that full length TPS1 alleles do not result in any trehalose synthesis in higher plants may be caused by the inhibitory effect of the N-terminus. Construction of transgenic plants with these N-terminally deleted constructs may result in plants with higher trehalose levels and better stress resistance.

Example 4

Construction of Transgenic Plants of *Arabidopsis thaliana*, Producing Trehalose The transformation of *Arabidopsis thaliana* ecotype Columbia is carried out by means of the vacuum infiltration method (Bechtold, N. et al., C. R. Acad. Sci. Paris 316: 1194-1199 (1993); Bent, A. et al., Science 265: 1856-1860 (1994)), using *Agrobacterium tumefasciens* C58C1 strain harboring the helper plasmid pMP90 and the appropriate plasmid construct, and is mobilized from *E. coli* strain DH5-alpha by triparental mating using *E. coli* strain HB101 harboring plasmid pRK2013 as a helper.

Briefly, *A. thaliana* plants are grown at 22-20° C., under 16 hrs light, for 4-6 weeks, until inflorescences are starting to appear. After pouring an *Agrobacterium* culture inside a vacuum desiccator, pots containing *Arabidopsis* plants are placed upside down and vacuum infiltrated for 5 min. Plants are allowed to grow under the conditions described above. Seeds are harvested and selected in Petri dishes containing 4.4 g/L MS salts, 1% sucrose, 0.5 g/L MES buffer pH 5.7 (KOH), 0.8% phytagar, and 30 mg/L kanamycin to select transformants. 500 mg/L carbenicillin are added as well to stop bacterial growth. After 5-7 days transformants are visible as green plants and transferred to the same medium as above but with 1.5% phytagar. After 6-10 days plants with true leaves are transferred to soil.

Analysis of transgenic plants is conducted to determine gene integration in the plant genome and gene copy-number by Southern blot and transcription of transgene is carried out by Northern blot by standard techniques (Sambrook, J. et al., Molecular cloning: A laboratory manual. Second Edition. Cold Spring Harbor Laboratory Press, New York (1989)). An antibody against Sl-TPS1 is used to confirm the correct translation of transgene using Western blot (Towbin, H. et al., Proc. Natl. Acad. Sci. USA 76, 4350-4353 (1979)). Trehalose-6-phosphate synthase activity (De Virgilio, C. et al., FEBS Lett. 273: 107-110 (1990)) and trehalose content (Neves, M J. et al., World J. Microbiol. Biotechnol. 10: 17-19 (1994)) were measured by known methods.

Table 4 shows the phentotypes of transgenic *Arabidopsis thaliana* overexpressing plant trehalose-6-P synthase gene.

using the *Agrobacterium tumefasciens* system and said technique can be set up in a laboratory by persons who master the state of the art. The constructs for the expression in plants of any plant trehalose-6-phosphate_synthase gene, preferably SlTPS1, devoid of its N-terminal region can be made in a vector derived from the Ti plasmid that lacks the T-DNA tumorigenic genes and which contains a selection marker for transformed plants that, for example, confers resistance to kanamycin (Bevan, M., 1984, Nucl. Acids Res. 22: 8711-8721). Furthermore, an appropriate promoter must be chosen depending on the use that will be given to the transgenic plants. The polyadenylation signal from the nopaline synthetase gene in the T-DNA can be used (Bevan, M., Barnes, W. and Chilton, M.-D., 1983, Nucl. Acids. Res. 11: 369-385).

To overproduce trehalose for industrial use, plants such as potato, sugarcane or sugarbeet, can be used. For instance, potato stores large amounts of carbohydrates in the tuber. In terms of the plant biomass, potato represents one of the most productive crops per unit of area (Johnson, V. A. and Lay, C. L., 1974, Agric. Food Chem. 22: 558-566). There are strong tuber-specific promoters such as the class-1 promoter of patatin gene (Bevan, M. et al., Nucl. Acids Res. 14: 4625-4638 (1986); Jefferson, R. et al., Plant Mol. Biol. 14: 995-1006 (1990)) that could be used to produce large amounts of trehalose. The convenience of using potato, sugarbeet or sugarcane as systems for overproducing trehalose is that these plants are human food and therefore trehalose isolated from them would be easily accepted by consumers. The trehalose obtained by overexpression in plants could be used to pre-

TABLE 4

PHENOTYPES OF TRANSGENIC *Arabidopsis thaliana* OVEREXPRESSING PLANT TREHALOSE-6-P SYNTHASE GENES.

| TRANSGENE | ROSETTE | GROWTH (FLOWERING TIME) | INFLORESCENCES | SEEDS | SILIQUA |
|---|---|---|---|---|---|
| AtTPS1 | Larger with green and some purple leaves | Delayed (1-2 weeks) | Larger | Normal | Normal |
| ΔNAtTPS1 | Smaller with many purple leaves | Delayed (2-3 weeks) | Larger | Fewer and purple | Normal on inflorescence tips and smaller and sterile on inflorescence bottoms |
| SlTPS1 | Smaller with green and some purple leaves | Delayed (1-2 weeks) | Larger | Normal | Normal |
| ΔNSlTPS1 | Smaller with many purple leaves | Delayed (2-3 weeks) | Larger | Fewer and purple | Normal on inflorescence tips and smaller and sterile on inflorescence bottoms |
| CONTROL | Normal | Normal | Normal | Normal | Normal |

Example 5

Mass Synthesis of Trehalose in Transgenic Potato, Sugarbeet and Sugarcane Plants Genetic engineering has made it possible to express almost any gene in a heterologous organism. Transgenic plants can be used as bioreactors for the large-scale production of compounds of commercial interest, that are normally only obtained in limited amounts, such as biodegradable plastics, different carbohydrates, polypeptides for pharmaceutical use and enzymes for industrial use (Goddijn, O. J. M. and Pen, J., Trends Biotech. 13: 379-387 (1995)). Different methods have been reported for the transformation of higher plants, including crops of great economic importance (Walden, R. and Wengender, R., Trends Biotech. 13: 324-331 (1995)). The transformation of tobacco (Horsch, R. B. et al., Science 227: 1229-1231 (1995)) and potato (Sheerman, S. and Bevan, M. W., Plant Cell Rep. 7: 13-16 (1988)) are efficiently carried out serve biomolecules for industrial use, such as restriction and modification enzymes (Colaço, C. et al., Bio/Technology 10: 1007-1111 (1992)), vaccines, or processed foods.

Example 6

Transgenic Cereal Plants Resistant to Environmental Stress

The cereals constitute the basic food for world nutrition and they could be cultivated under unfavourable weather conditions if they could produce trehalose in response to cold, heat, salinity or drought. In order to achieve this, it is required to express any plant trehalose-6-phosphate_synthase gene, preferably Sl-TPS1, devoid of its N-terminal region under the control of promoters that are induced by any of these environmental factors (Baker, S. S. et al., Plant Mol. Biol. 24: 701-713 (1994); Takahashi, T. et al., Plant J. 2: 751-761 (1992); Yamaguchi-Shinozaki, K. and Shinozaki, K., Plant Cell 6: 251-264 (1994)). The synthesis of trehalose only under stress conditions would avoid the continuous production of trehalose (using a constitutive promoter) which diverts the carbohydrate metabolism and as a consequence could decrease the quality and productivity of grains. There are reports on transformation of maize (D'Halluin, K. et al., Plant Cell 4: 1495-1505 (1992)), barley (Wan, Y. and Lemaux, P. G., Plant Physiol. 104: 37-48 (1994)), wheat (Vasil, V. et al., Bio/Technology 10: 667-674 (1992)) and rice (Shimamoto, K. et al., Nature 338: 274-276 (1989)). This methodology can be implemented by a person familiar with the state of the art.

Example 7

Fruit from Transgenic Plants with a Longer Shelf Life

Different types of fruit such as tomato, mango and banana ripen quickly and tend to rot before they reach consumers. The early harvesting of fruits and their storage in refrigeration or in chambers with a controlled environment has been traditionally used to avoid this problem. However, these methods are expensive, especially if the fruits will be transported to distant places. In order to increase the shelf life of tomato, a delay in ripening has been reported using transgenic plants that express in antisense the polygalacturonase gene which is involved in fruit ripening. In spite of this delay in ripening, there is still the problem that after a certain time this process is carried out without the product necessarily reaching the consumer in a good state.

As an alternative to this method, it is here proposed to produce trehalose in transgenic tomato, mango and banana plants. For example, using a specific promoter of the tomato fruit (Bird, C. R. et al., Plant Mol. Biol. 11: 651-662 (1988)), any plant trehalose-6-phosphate synthase gene, preferably Sl-TPS1, devoid of its N-terminal region could be overexpressed so that trehalose accumulates specifically in that organ. The method of transformation and regeneration for tomato plants (as described by McCormick, S. et al., Plant Cell Rep. 5: 35 81-84 (1986)) can be carried out by any person who knows that state of art. Tomato and other types of fruit could be harvested ripe and then submitted whole or in parts to desiccation and preserved for long periods without the need for refrigeration. When rehydrated, the fruit would have the normal organoleptic properties that the consumer demands. In principle, the strategy described above can be implemented for other types of fruit provided a regeneration and transformation system is available for the plant in question and that there is an appropriate fruit-specific promoter.

Example 8

Increase in the Viability of Cells, Organs or Plant Parts Involved in Sexual or Asexual Reproduction The production of pollen with prolonged viability would be of great help in plant breeding programs and in the preservation of germplasm. Similarly, the possibility of storage for long periods and an increase in the viability of seeds, bulbs, tubers, cuttings for grafts, sticks and flowers will have a great impact on plant breeding and the conservation of germplasm. The presence of trehalose in a tissue, organ or part of the transformed plant will make it possible to preserve said tissue, organ or part at room temperature in a dehydrated state for significantly greater periods than without trehalose. In order to achieve this objective, it is necessary to clone any plant trehalose-6-phosphate_synthase gene, preferably Sl-TPS1, devoid of its N-terminal region into a plant expression vector under a tissue-specific or organ-specific promoter and transform the plant in question with this construct by any of the reported methods known to someone familiar with the state of art. There are reports of pollen-specific promoters. (Guerrero, F. D. et al., Mol. Gen. Genet. 224: 161-168 (1990), tuber-specific promoters (Bevan, M. et al., Nucl. Acids Res. 14: 4625-4638 (1986); Jefferson, R., Plant Mol. Biol. 14: 995-1006 (1990)) and seed-specific promoters (Colot, V. et al., EMBO J. 7: 297-302 (1988)) that could be used to construct hybrid genes for the expression of trehalose in plants.

Example 9

Testing of Different Stress Conditions

The tolerance of the transgenic plants against various stress conditions was tested in the following manner.

1. Cold

Transgenic plants overexpressing Sl-TPS1 under control of the constitutive 35S promoter were analyzed by Southern blot to verify correct transgene insertion in the plant genome. Sl-TPS1 gene expression was corroborated by Northern blot. Transgenics were checked to accumulate trehalose and not detected in control plants, transformed only with the vector. Transgenic *Arabidopsis* T2 generation plants (20 days old) were grown in pots containing soil/vermiculite, under 16 hr light/8 hr dark at 24° C. in a growth chamber under well-watered conditions. Control and trehalose-synthesizing plants were transferred to a growth chamber at 4° C. for 10 days at constant light and returned to 24° C. for 2 days. Other sets of plants were left at 24° C. Damage in cold-treated plants was estimated visually (chlorosis, leaf deterioration and death) and by measuring photoinhibition of photosynthesis (Murata, N. et al., Nature 356: 710-713 (1992)) using an IRGA (infrared gas analyzer) apparatus. Also growth retardation was measured in leaf size ad plant hight after comparison of cold-treated plants vs. non-treated.

2. Freezing

Freezing tolerance was determined in cold-treated control and trehalose-synthesizing plants, obtained as previously described, by the electrolyte leakage test. Detached leaves were frozen to various subzero temperatures and, after thawing, cellular damage due to membrane lesions was estimated by measuring ion leakage from the tissues using a conductivity meter (Jaglo-Ottosen, K. R. et al., Science 280:104-106 (1998).

3. Heat

Transgenic *Arabidopsis* T2 generation plants (20 days old), control and trehalose-synthesizing were grown in pots containing soil/vermiculite, under 16 hr light/8 hr dark at 24° C. in a growth chamber under well-watered conditions. Plants were preacconditioned after incubation for two hr at 35° C. and then subjected to 1 hr of heat stress at various temperatures ranking from 46 to 56° C. for each independent treatment. Plants were returned to 24° C. for 5 days. Damage was determined visually (chlorosis, leaf deterioration and death). Similar tests can be conducted using plantlets grown for 7 days at 24° C. on moisted filter paper inside Petri dishes (Lee, J. H. et al., Plant J. 8: 603-612 (1995)).

4. Dessication

Transgenic *Arabidopsis* T2 generation plants (20 days old), control and trehalose-synthesizing were grown in pots containing soil/vermiculite, under 16 hr light/8 hr dark at 24° C. in a growth chamber under well-watered conditions. Drought stress was imposed by stopping the watering for several days until the leaves were wilted and then the plants were rewatered. Controls did not recover whereas trehalose-producing plants continued growing normally. Also detached leaves were air-dried at 20% relative humidity. The fresh weight was measured over a 48-hr period. Trehalose-producing plants lost less weight (Holmstrom, K.-O. et al., Nature 379: 683-684 (1996)).

5. Osmotic Stress

Transgenic *Arabidopsis* T2 generation plants (20 days old), control and trehalose-synthesizing were grown in pots containing soil/vermiculite, under 16 hr light/8 hr dark at 24° C. in a growth chamber under well-watered conditions. Independent sets of plants were irrigated with various concentrations of NaCl (100-300 mM) or PEG (5 or 10%) during 1-3 weeks. Plant growth was evaluated by measuring the percent of change in height and in fresh weight (Tarczynski, M. C. et al., Science 259:508-510 (1993)).

6. Storage

The plant TPS gene will be cloned under the control of for instance the tomato fruit-specific E8 promoter which is induced by ethylene and its maximum activity is reached in mature fruits (Lincoln, J. E. & Fischer, R. L., Mol. Gen. Genet. 212: 71-75 (1988); Good, X. et al., Plant Mol. Biol. 26:781-790 (1994); Tieman, D. et al., Plant Cell 4:667-679 (1992)) in pBIN19 vector containing a NOSpA 3' end (Guilley, H., et al., Cell 21: 285-294 (1982)) and (Bevan, M. et al., Nucl. Acids Res. 11: 369-385 (1983)). The vectors will be mobilized to *Agrobacterium tumefaciens* by triparental mating. Tomato transformation will be performed by well established protocols (Tieman, D. et al., Plant Cell 4: 667-679 (1992)). Transgenic fruit analysis will be carried out using different techniques. Determination of Sl-TPS1 cDNA integration in the plant genome by genomic Southern gels. Determination of Sl-TPS1 transcription by Northern blotting and Sl-TPS1 protein expression by Western blotting. Measurement of Sl-TPS1 enzyme activity and trehalose content will be performed by standard techniques (De Virgilio, C. et al., FEBS Lett. 273: 107-110 (1990) and (Neves, M J. et al., World J. Microbiol. Biotechnol. 10: 17-19 (1994)). Shelf-life is analyzed in control and trehalose-producing tomatos considering several maturation parameters, such as: Softening ratio, ethylene production and fruit quality (texture, colour, sugar content, size) over several weeks period.

Example 10

Trehalose-6-phosphate Assay 1.1 Existing Trehalose-6-phosphate Assays

To study the importance of Tps1 and more specifically of it's product trehalose-6-phosphate, it is essential to be able to measure the Tre6P levels that are effectively present in the cytosol. Until now three methods have been described to determine Tre6P levels. In a first method (Meleiro et al., 1993, *Analytical Biochemistry* 213, 171-2) Tre6P was extracted by a combination of TCA extraction, followed by ether extractions, barium acetate precipitations and anion exchange chromatography. The Tre6P was dephosphorylated by alkaline phosphatase, hydrolysed into two glucose molecules by trehalase and finally the glucose was detected by the glucose oxidase—peroxidase method. This method has been developed to evaluate a procedure to produce and purify large quantities of Tre6P. Since the reported Tre6P levels in yeast cells are lower than the glucose, trehalose and Glu6P levels, this method would have an enormous background and lack of sensitivity.

A second method uses High Pressure Liquid Chromatography (HPLC) to detect and quantify Tre6P (De Virgilio et al., 1993, *Eur J Biochem* 212, 315-23). With this method it was possible to quantify high Tre6P levels in tps2Δ mutants after a heat-shock (Reinders et al., 1997, *Mol Microbiol* 24, 687-95) and detect a transient increase in Tre6P levels after the addition of glucose to derepressed wild type yeast cells (Hohmann et al., 1996, *Mol Microbiol* 20, 981-91). It had a detection limit of around 200 μM Tre6P. This is around the steady state levels that have been reported in exponentially growing and stationary phase cells (Blazquez et al., 1993, *FEBS Lett* 329, 51-4). The sensitivity of this method does not allow reliable quantification of concentrations present in normal yeast strains or strains affected in Tre6P synthesis.

A third method is based on the observation that Tre6P inhibits yeast hexokinase activity in vitro (Blazquez et al., 1994, *FEMS Microbiol Lett* 121, 223-7). The level of this inhibition serves as a measure for the Tre6P content of the extracts. Hexokinase activity is measured by determining the formation rate of one of its products, fructose-6-phosphate (Fru6P). The intracellular Tre6P in stationary and exponentially growing cells was estimated to be around 200 μM. The authors also observed that this inhibitory effect of Tre6P on hexokinase activity was suppressed by the presence of glucose. Since in certain conditions, high concentrations of glucose and in general other interfering compounds may be present in the extracts, this method is also not suitable.

1.2 Principles of the Novel Method

The method of the invention has as prime objective to be more sensitive and more reliable than the existing methods. It is based on the *Bacillus subtilis* phosphotrehalase enzyme that is encoded by the treA gene. This enzyme is functionally related to the bacterial PTS system, and hydrolyses Tre6P into glucose and Glu6P (Helfert et al., 1995, *Mol Microbiol* 16, 111-120; Rimmele & Boos, 1994, *J Bacteriol* 176, 5654-64). By measuring the glucose produced in this reaction, the initial amount of Tre6P can be calculated. Glu6P is not used for this purpose because this compound is often present in large amounts in yeast cells. It is difficult to separate it from Tre6P, while the glucose originally present in the extracts can easily be separated from the sugar phosphates by anion exchange chromatography (FIG. 16).

1.3 Purification of the *B. subtilis* Phosphotrehalase Enzyme

The phosphotrehalase enzyme has been purified and characterised by the group of M. K. Dahl (Gotsche & Dahl, 1995, *J Bacteriol* 177, 2721-6; (Helfert, et al., 1995, supra). This group provided the pSG2 plasmid with the treA gene expressed constitutively behind the strong *B. subtilis* degQ36 promotor.

Figure 7:
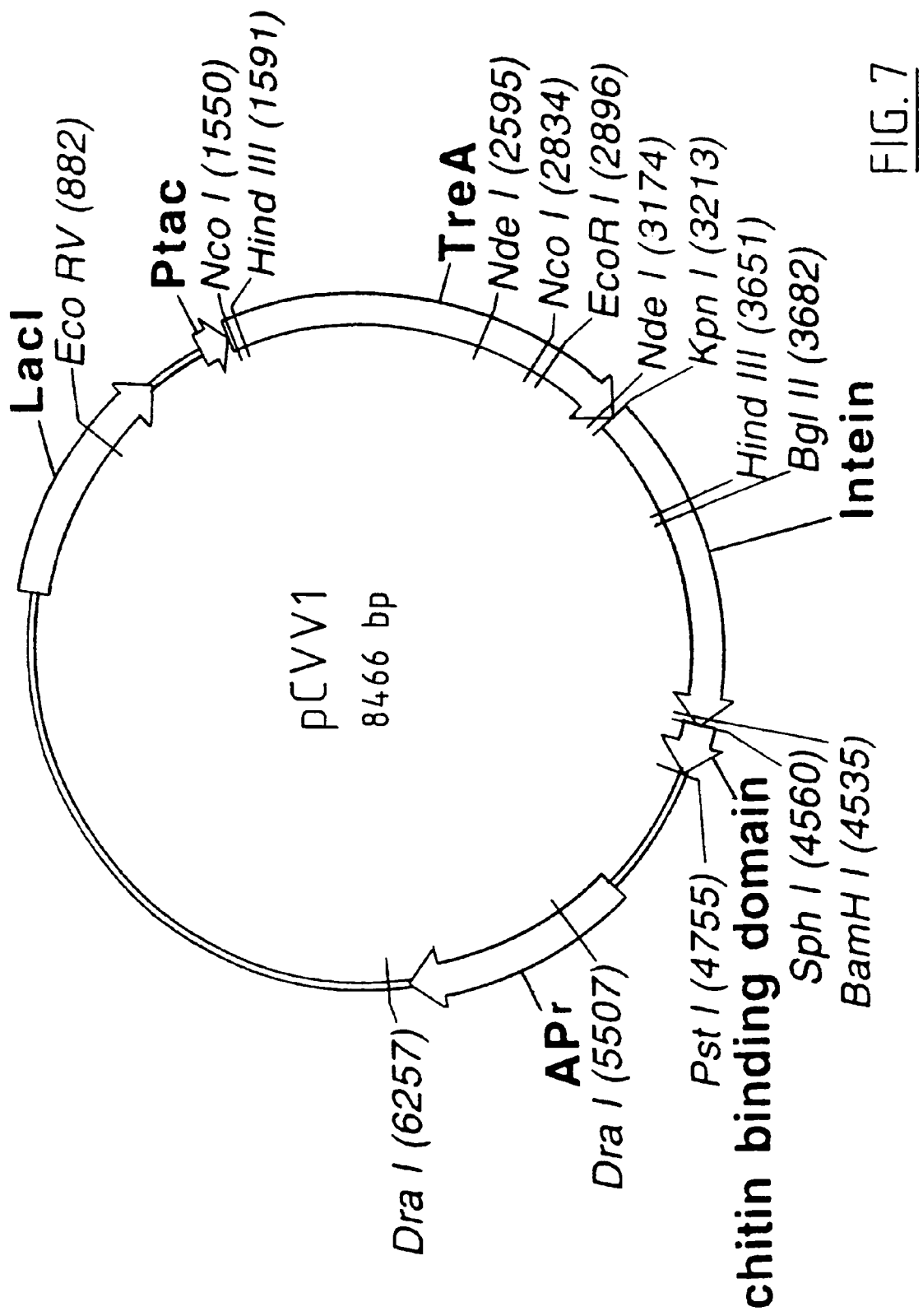
FIG. 7 is a structural diagram of pCVV1.

To obtain high stable expression, the gene was cloned in the pCYB1 vector (New England Biolabs) behind the strong IPTG inducible tac promoter. The treA gene was PCR amplified with the primers CVV5 (TGGTGGATTA,ATATGAAAACA-GAACAAACGCCATGGTGG) (SEQ ID NO: 13) and CVV6 (TTAACAGCTCTTCC'GCA,AACGATAAACAATGGACTCATATG GGCG) (SEQ ID NO: 14), introducing respectively an AseI and a SapI restriction site at each end of the PCR product and cloned in the pCYB1 plasmid and called pCVV1 (FIG. 7), and, indicate the site where the restriction enzyme splices.

Figure 17:
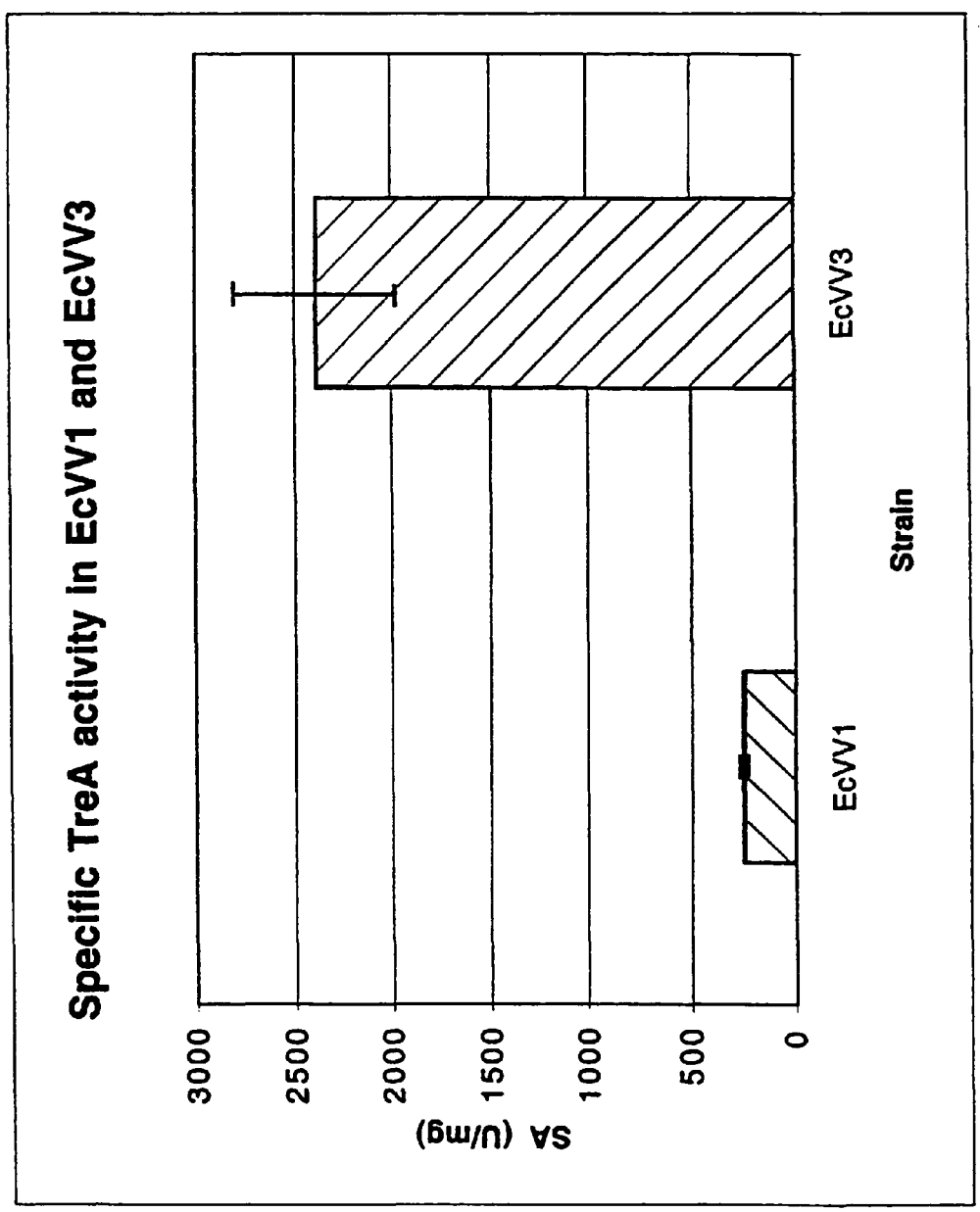
FIG. 17 is a bar graph showing a comparison of specific phosphotrehalase activity in strains EcVV1 and EcVV3.

Comparison of the phosphotrehalase activity of the strains transformed with the original pSG2 plasmid (EcVV1) or the new pCVV1 (EcVV3) showed that the latter strain contained 10 times more activity than the strain with the pSG2 plasmid (FIG. 17).

These EcVV3 cells were grown overnight in 4 ml LB-ampicilin medium. The next day this culture was used to inoculate 100 ml LB ampicilin and was left to grow again for 3 hours wherafter expression was induced with IPTG (0.5 mM) and the culture incubated for another 3 hours at 37° C.

Cells were centrifuged 10 minutes at 4000 rpm and resuspended in 30 ml buffer A (25 mM Bis-Tris pH 7, 10 mM KCl, 1 mM CaCl$_2$, 1 mM MgCl$_2$). The cells were broken by passing the resuspended cells twice through a French press. The crude extract was then cleared by ultracentrifugation for 30 minutes at 35000 rpm and the supernatant was passed through a 0.22 µm filter.

The anion exchange chromatography was performed with a linear gradient from 100% buffer A to 50% buffer B (25 mM Bis-Tris pH 7, 10 mM KCl, 1 mM CaCl$_2$, 1 mM MgCl$_2$, 1M NaCl) in 20 column volumes on a MonoQ HR5/5 column. Fractions of 500 µl were collected. The PNPG hydrolysing activity of each fraction was measured and the two fractions with the highest activity were pooled and concentrated to 200 µl before the gelfiltration with a Vivaspin column (Vivascience). For the gelfiltration an isocratical elution with 10% buffer B was used on a Superdex75 column. The two 500 µl fractions with the highest activity were pooled and concentrated again to 400 µl and stored in aliquots at −30° C. Both columns were run on a ĀKTA-FPLC system (Pharmacia).

The purification performed in this way gave a 4,5 fold increase in specific activity with a recovery of 34%. SDS-PAGE analysis with Coomassie Blue staining showed already a huge overexpression protein band from the expected size. No other bands were visible in the final purified fractions with 10 µg protein per lane.

1.4 Sampling of the Yeast Culture

Samples were taken by spraying 3 ml of a cell suspension into 10 ml of 60% methanol at −40° C. This immediately arrests cell metabolism and allows determination of the intracellular metabolites as a function of time after an experimental manipulation, e.g. adding glucose to derepressed cells (de Koning & van Dam, 1992, *Anal Biochem* 204, 118-23).

1.5 Extraction of Metabolites

The extraction of metabolites of the frozen cells was performed using perchloric acid extraction.

1.6 The First Anion Exchange Chromtography

To separate the glucose and trehalose from the Tre6P present in the cell extracts, the weak NH2-SPE anion exchanger (International Sorbent Tenchnology, UK) was selected.

The columns were filled with 500 mg of sorbent resuspended in 3 ml of 100% methanol and rinsed with 3 ml 100% methanol. A weak anion was bound to it by equilibrating the column with 0.5 M acetic acid and the excess of acid in the column was rinsed away with 2 times 3 ml of MilliQ water. The sample was applied and the bound sample was rinsed with 3 ml of 20% methanol to eliminate aspecific binding. The anions were eluted with a 2.5 M ammonia solution pH 12.5. When 250 mg of sorbent was used per 100 mg of cells extracted there was no risk of overloading the column. The salt did not interfere significantly with the glucose determination. The eluted extracts were evaporated without loss of Tre6P.

1.7 The Phosphotrehalase Reaction Conditions

Because the enzyme was unstable at the reported pH optimum of 4.5, a more physiological pH of 7 was choosen to perform the incubation. The incubation buffer was a 50 mM Bis-Tris buffer pH7. The incubation temperature was 37° C. 2000 U of phosphotrehalase were added and the samples incubated at 37° C. for 2 hours. One unit was the amount of enzyme that hydrolysed 1 nmol of Tre6P per minute in the conditions mentioned.

1.8 The Second Anion Exchange Chromtography

To separate the glucose that was produced in the phosphotrehalase reaction from the other anionic cell compounds a second anion exchange chromatography was performed in the same way as the first one. This time the flow-through that does not bind to the column and that contains the glucose, was recovered and concentrated by vacuum drying.

1.9 The Glucose Assay

The dried glucose samples were redissolved in 250 µl 50 mM Bis-Tris buffer pH7. From each sample the glucose concentration was determined in 200 µl undiluted sample and in a ⅕ and ½5 dilution. In a microtiter plate to a sample volume of 200 µl, 20 µl of a reaction mix containing 15 units glucose oxidase, 10 units of peroxidase and 100 µg ortho-dianisidine was added. This plate was incubated at 37° C. for 45 minutes and then the reactions were stopped by adding 40 µl of 56% sulfuric acid. The absorbance was measured at a wavelength of 530 nm.

1.10 Recovery and Reproducibility

The recovery of the perchloric acid extraction procedure is 57%. The recovery of the complete Tre6P assay is 25%. The detection limit of the method was 100 µM and Tre6P standard lines are linear in the physiologically relevant range (FIG. 8). The Tre6P standards were made by adding known amounts of Tre6P to cells of the tps1 Δ strain that lacks the Tre6P synthase, before the perchloric acid extraction. The standard error on the slope and intercept of 4 independent standard lines was respectively 2 and 9%.

The trehalose-6-phosphate concentrations were measured in yeast strains containing the full length and N-terminally deleted plant TPS1 alleles. The strains were either grown till exponential phase or till stationary phase in either galactose or glucose containing minimal medium. For this experiment tps1Δtps2Δ backgrounds were used because the level of trehalose-6-P in tps1Δ backgrounds is too low to be measured. The strains that were used are:

JT6308 1Δ2Δ+pSAL4

PVD44 1Δ2Δ+pSAL4/Sc TPS1

JT6309 1Δ2Δ+pSAL4/Sl TPS1

PVD43 1Δ2Δ+pSAL4/ΔN Sl TPS1

PVD138 1Δ2Δ+PSAL6/At TPS1

JT20050 1Δ2Δ+pSAL6/ΔN At TPS1

PVD150 2Δ+pRS6 (empty plasmid with HIS3 marker)

"1Δ" stands for "tps1Δ", "2Δ" stands for "tps2Δ".

Figure 18:
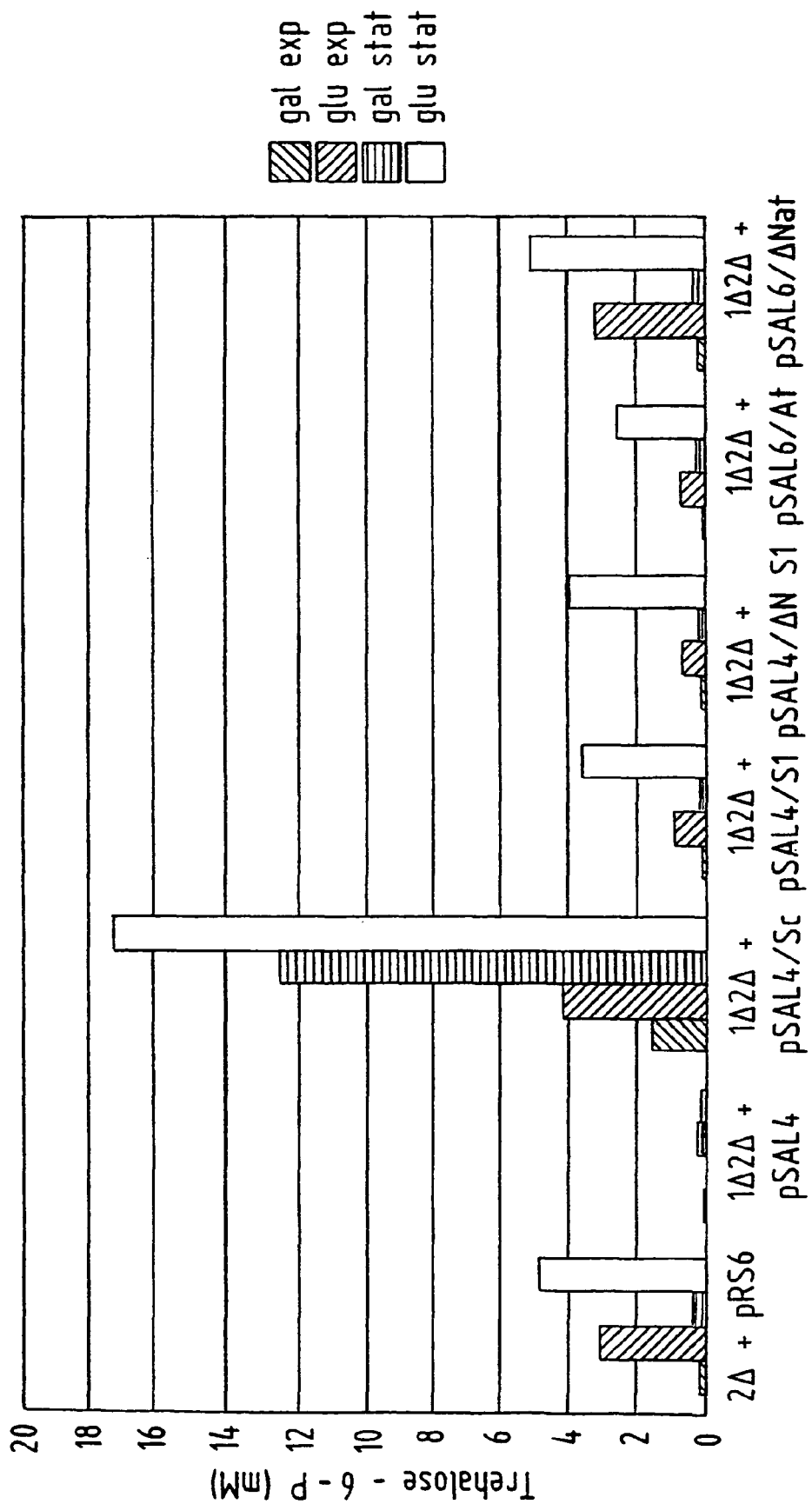
FIG. 18 is a bar graph showing the results of trehalose-6-phosphate measured in extracts from collected yeast cells.

After collecting the yeast cells, extracts were made as described in example 10 and trehalose-6-P concentrations were measured. The results are shown in FIG. 18.

There is four times less trehalose-6-phosphate in the extracts prepared from the strains containing the plant TPS1 genes compared to the control strain overexpressing the yeast TPS1 gene. This lower trehalose-6-phosphate level might explain why there is still deregulation of the glucose influx in glycolysis in these strains (example 12). This deregulation of glucose influx was similar for strains containing either the full length or the N-terminally deleted plant TPS alleles and this fits with the results that we have obtained here. There is no difference in trehalose-6-phosphate levels between strains containing the full length or the N-terminally deleted alleles.

Example 11

Chimaeric Fusions of TPS and TPP Domains

To generate a more efficient enzymatic pathway involved in trehalose biosynthesis a series of chimaeric enzyme fusions were created between TPS and TPP domains from TPS1 and TPS2 either from *A. thaliana* or *S. cerevisiae*. As shown in FIG. 13, these four fusions consist of: a 1337 by DNA fragment from AtTPS1 ( )NAtTPS1) encoding a N-terminus truncated protein (lacking its first 100 amino acids) of 442 amino acids, obtained by PCR (94° C., 3 min, 1 cycle; 94° C., 1 min, 52° C., 1 min, 72° C., 1.5 min, 40 cycles; 72° C., 10 min, 1 cycle) using Expand High-fidelity DNA polymerase (Boehringer) with oligonucleotides (5'-CATG-CCATGGCTTAT-AATAGGCAACGACTACT-TGTAGTG-3' (SEQ ID NO: 6), underlined NcoI site and bold initiation codon) and (5'-CG GGATCCAGCTGTCATGTTTAGGGC-TTGTCC-3' (SEQ ID NO: 15), underlined BamHI site), fused to a 1138 by DNA fragment from AtTPPB encoding the full-length protein of 374 amino acids obtained by PCR (94° C., 3 min, 1 cycle; 94° C., 1 min, 52° C., 1 min, 72° C., 1.5 min, 40 cycles; 72° C., 10 min, 1 cycle) using Expand High-fidelity DNA polymerase (Boehringer) with oligonucleotides (5'-CG GGATCCACTA-ACCAGAATGTCATCG-3' (SEQ ID NO: 16), underlined BamHI site) and (5'-GG GGTACCTCACTCTT-CTCCCACTGTCTTCC-3' (SEQ ID NO: 17), underlined KpnI site and bold stop codon).

A second fusion consists of) NAtTPS1 fused to a 1358 by DNA fragment from ScTPS2 encoding 397 amino acids from its C-terminus, obtained by PCR (94° C., 3 min, 1 cycle; 94° C., 1 min, 50° C., 1 min, 72° C., 1.5 min, 40 cycles; 72° C., 10 min, 1 cycle) using Expand High-fidelity DNA polymerase (Boehringer) with oligonucleotides (5'-CG GGATCCGCTAAATCT-ATTAACATGG-3' (SEQ ID NO: 18), underlined BamHI site) and (5'-CGG GGTACCATGG-TGGGTTGAGAC-3' (SEQ ID NO: 19), underlined KpnI site).

A third construct led to a fusion between a 1531 by DNA fragment from ScTPS1 encoding for a 492 amino acid protein, obtained by PCR (94° C., 3 min, 1 cycle; 94° C., 1 min, 52° C., 1 min, 72° C., 1.5 min, 40 cycles; 72° C., 10 min, 1 cycle) using Expand High-fidelity DNA polymerase (Boehringer) with oligonucleotides (5'-CCG CTCGAGGGTACTC-ACATACAGAC-3' (SEQ ID NO: 20), underlined XhoI site) and (5'-CG GGATCCGGTGGCA-GAGGAGCTTGTTGAGC-3' (SEQ ID NO: 21), underlined BamHI site), and AtTTPB.

The last fusion was made between ScTPS1 and ScTPS2 DNA fragments obtained as described above.

The PCR fragments were digested with appropriate restriction enzymes (FIG. 13) and subcloned in pRS6 vector. Yeast tps1Δ, tps2Δ and tps1Δtps2Δ mutant strains were transformed and selected in SDGal (-his). Complementation was assayed in SDGlc (-his minimal medium) and growth at 38.3° C.

Example 12

Expression in Yeast tps1Δ Strains, of N-terminally Deleted Plant TPS1 Genes, Restores the Growth on Glucose but does not Suppress Hyperaccumulation of Sugar Phosphates Deletion of TPS1 in *S. cerevisiae* results in a pleiotropic phenotype (Van Aelst et al., Mol. Microbiol., 8, 927-943, 1993). One of the phenotypes is that such a strain can not grow anymore on rapidly fermentable sugars. Why tps1Δ strains can not grow on glucose is not yet clarified. Three different hypotheses have been proposed (Hohmann and Thevelein, Trends in Biol. Sciences, 20, 3-10, 1995). When tps1Δ strains are shifted from a glycerol to glucose containing medium there is a rapid accumulation of sugar phosphates and a rapid drop in ATP concentration. Apparently the TPS1 gene has a function in the control of glucose influx into glycolysis. Because transport and phosphorylation are coupled, all the sugar that is coming into the cell is phosphorylated. Reducing the Hxk2 activity can suppress the growth defect phenotype of tps1Δ strains on glucose and fructose (Hohmann et al., Current genetics 23, 281-289, 1993). In vitro studies have clearly indicated that the product of the Tps1 protein, trehalose-6-phosphate, inhibits the activity of Hxk2 and as such, could control the flux of glucose into glycolysis.

When the *S. lepidophylla* homologue of TPS1 was expressed in yeast, a clear difference is seen in growth on glucose containing medium between the full length clone and the N-terminal deletion construct. Tps1Δ strains transformed with the full length Sl TPS1 under the control of the CUP1 promoter do not grow on glucose. Expression in a tps1Δ strain of a construct where the first 300 bp encoding the first 100 amino acids of the Sl Tps1 protein are deleted results in growth on glucose. So apparently, the full-length clone can not solve the glucose influx problem, whereas the N-terminal deletion is able to control the glucose influx.

To test this, an experiment was performed where the concentration of the first metabolites in glycolysis was measured. The following strains were used:

PVD72 Tps1Δ+pSAL4

PVD14 Tps1Δ+pSAL4/Sc TPS1

PVD73 Tps1Δ+pSAL4/Sl TPS1

PVD15 Tps1Δ+pSAL4/ΔN Sl TPS1

For the determination of the glycolytic metabolites, cells were grown on SDglycerol medium till exponential phase. Cells were harvested by centrifugation. The pellet was washed once, resuspended and then incubated in YP medium at 30° C. Glucose was added to a final concentration of 100 mM and $CuSO_4$ was added to a final concentration of 100 μM.

Before and after the addition of glucose, samples were taken at the time intervals indicated and immediately quenched in 60% methanol at −40° C.

Figure 14:
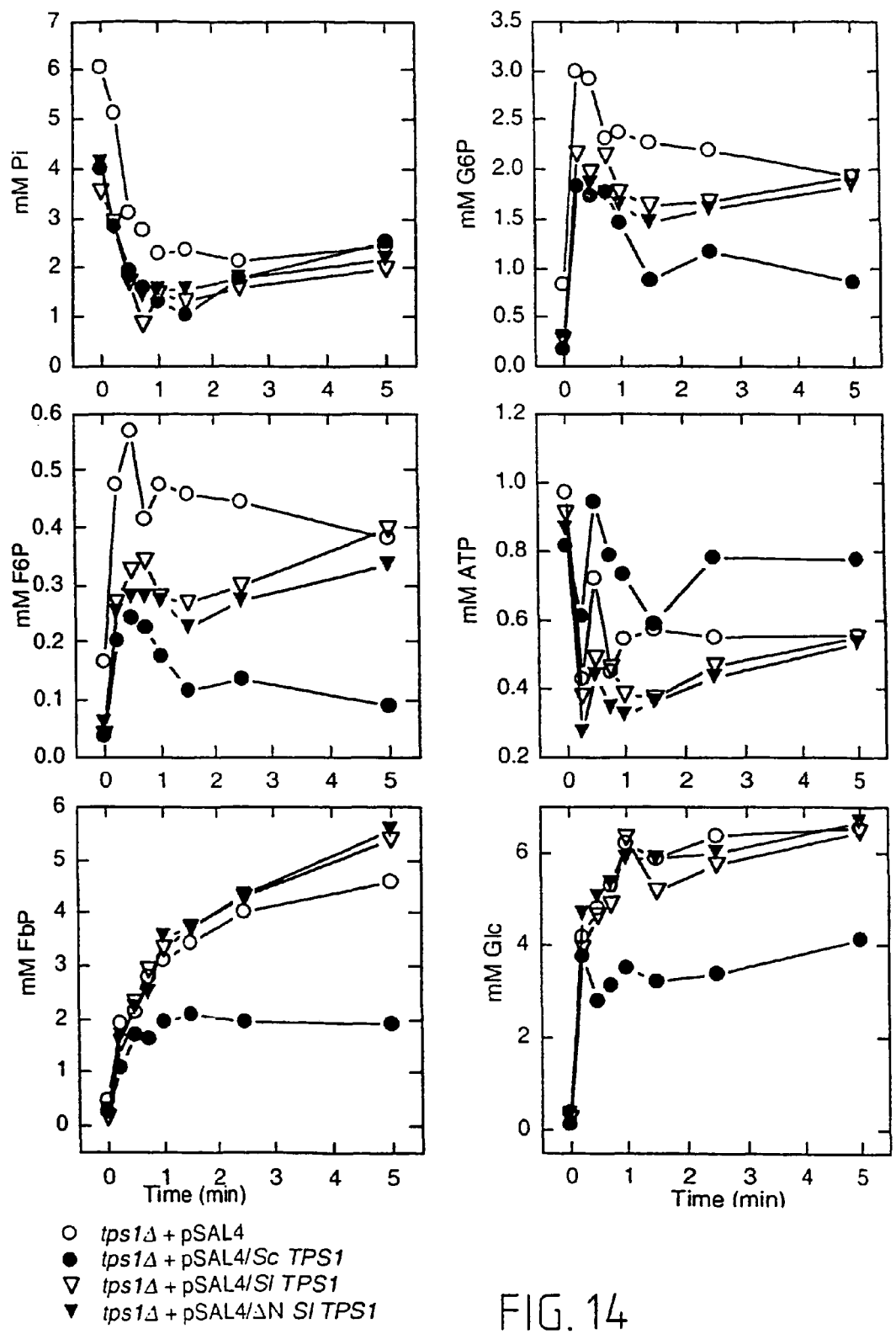
FIG. 14 is a graph of concentrations of glycolytic metabolites with respect to time.
Figure 15A:
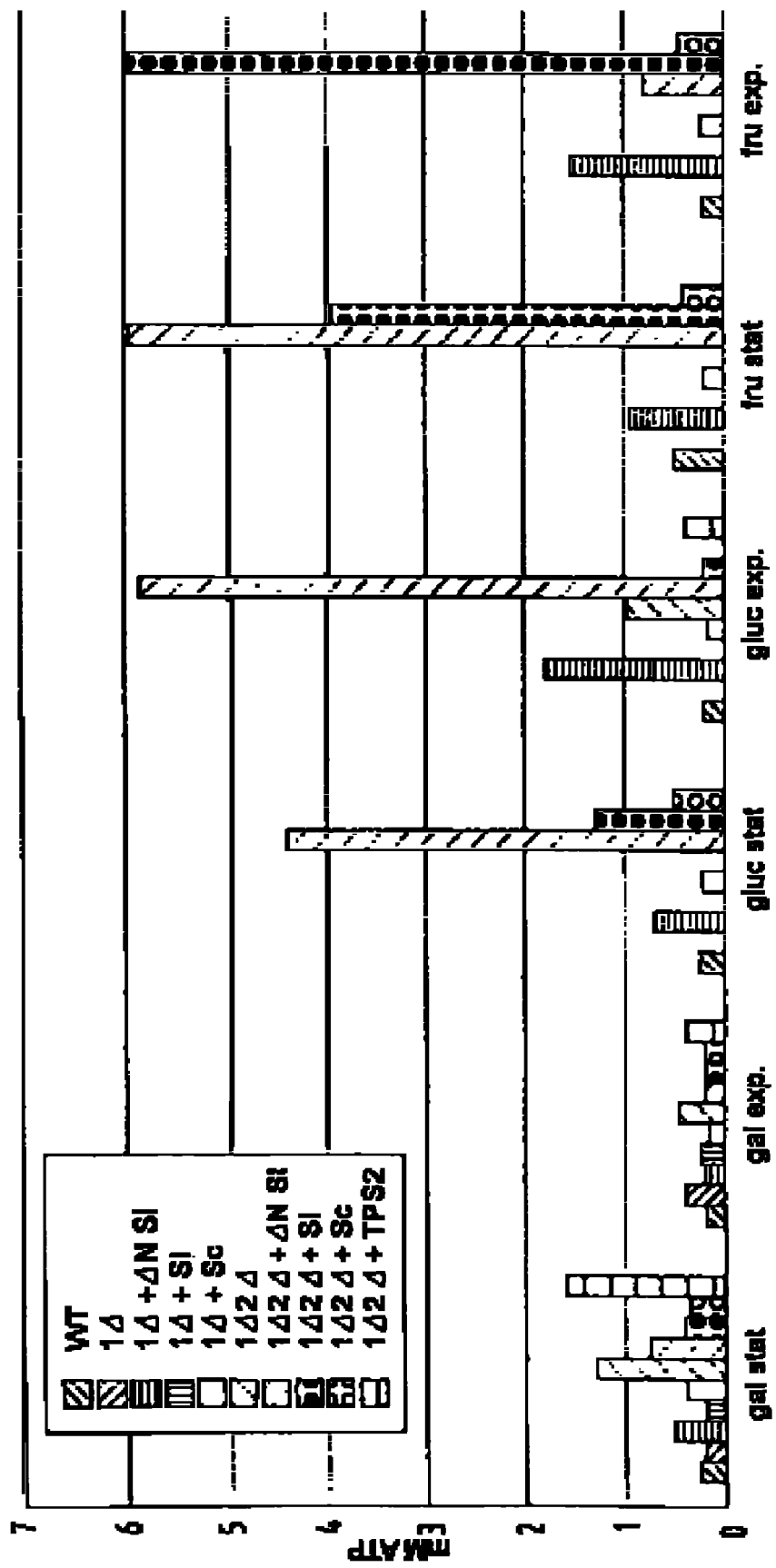
FIG. 15 is a graph of concentrations of metabolite concentrations measured during exponential growth and stationary phase.
Figure 15B:
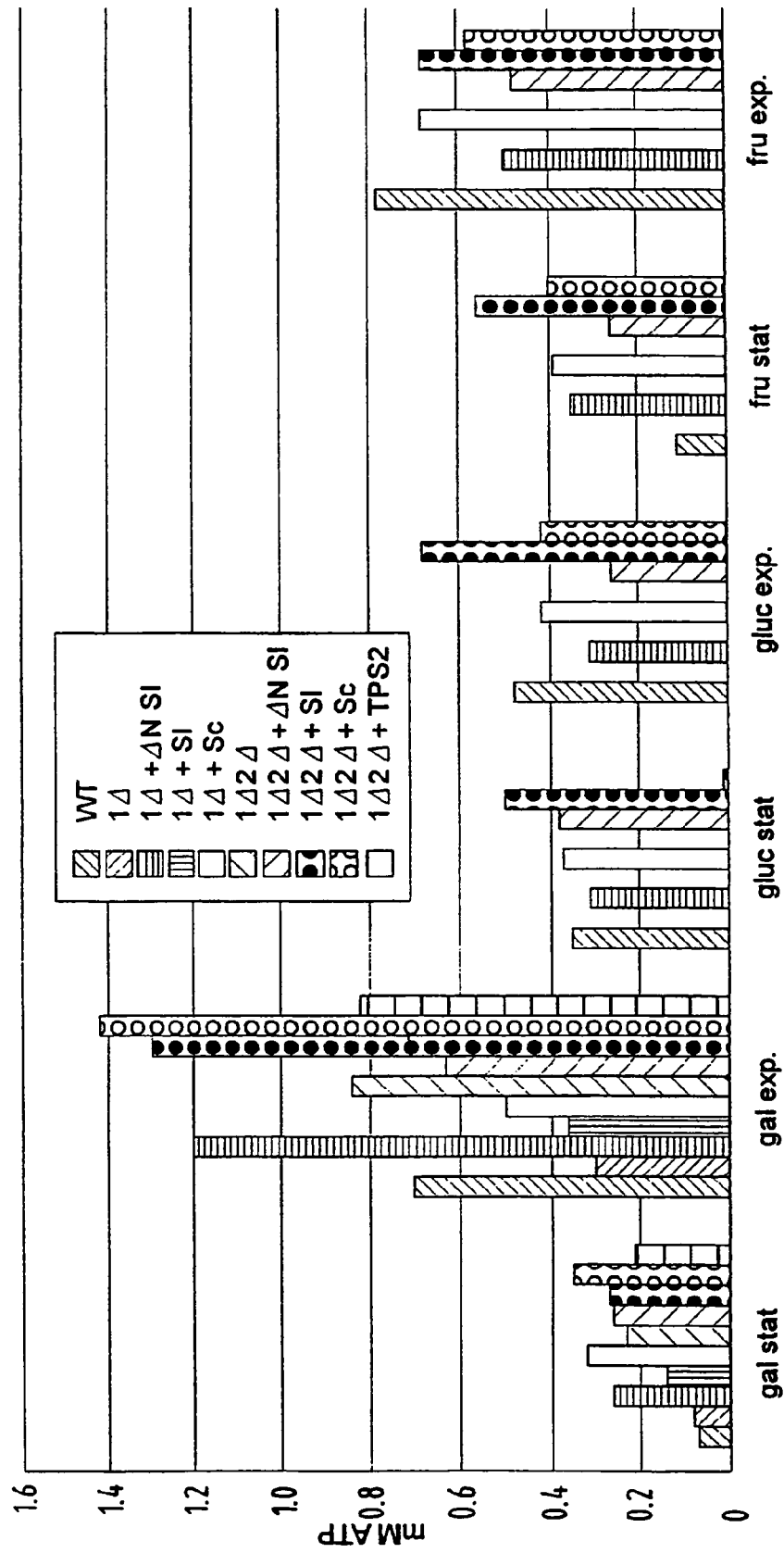
Figure 15C:
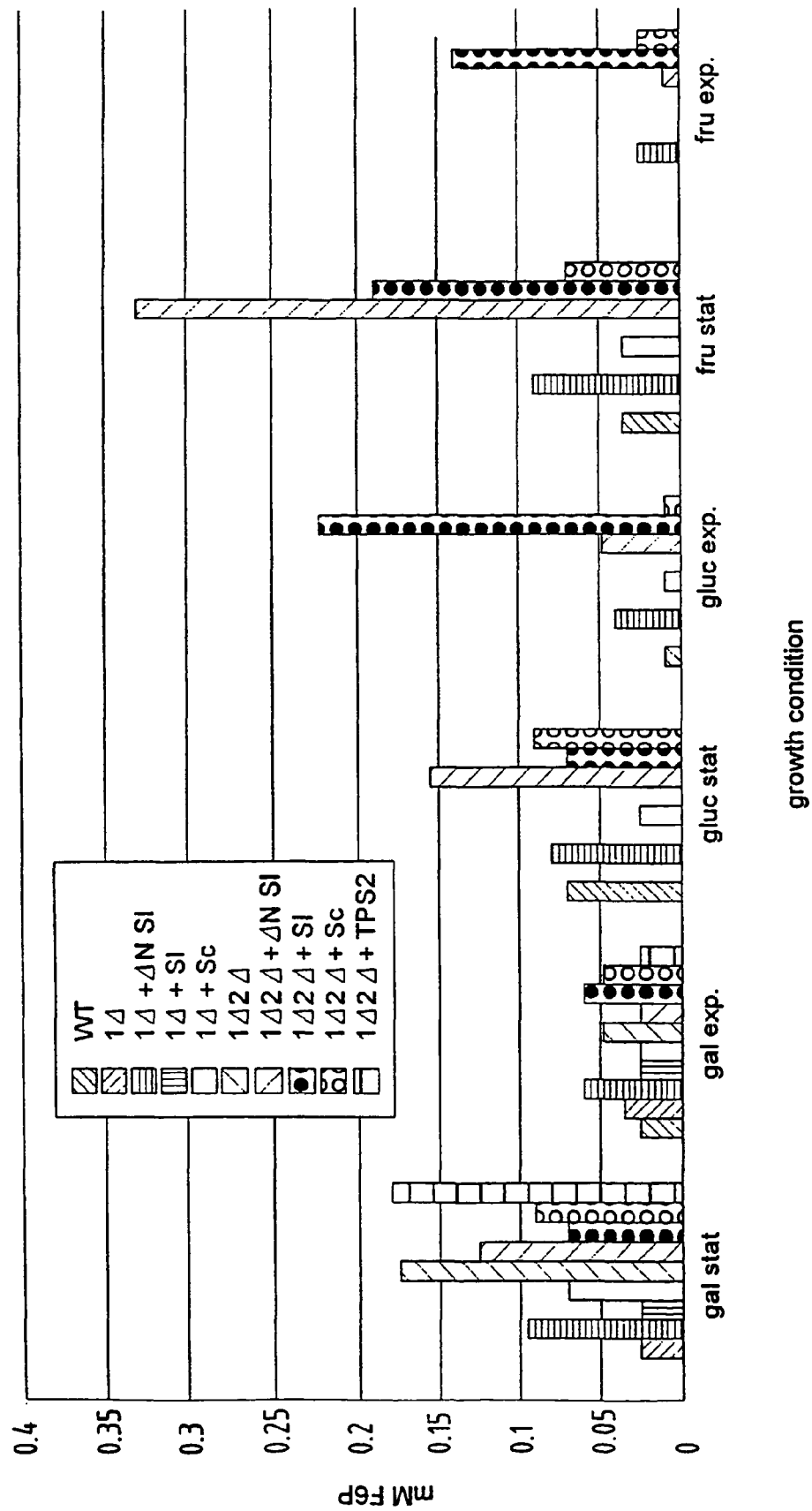
Figure 15D:
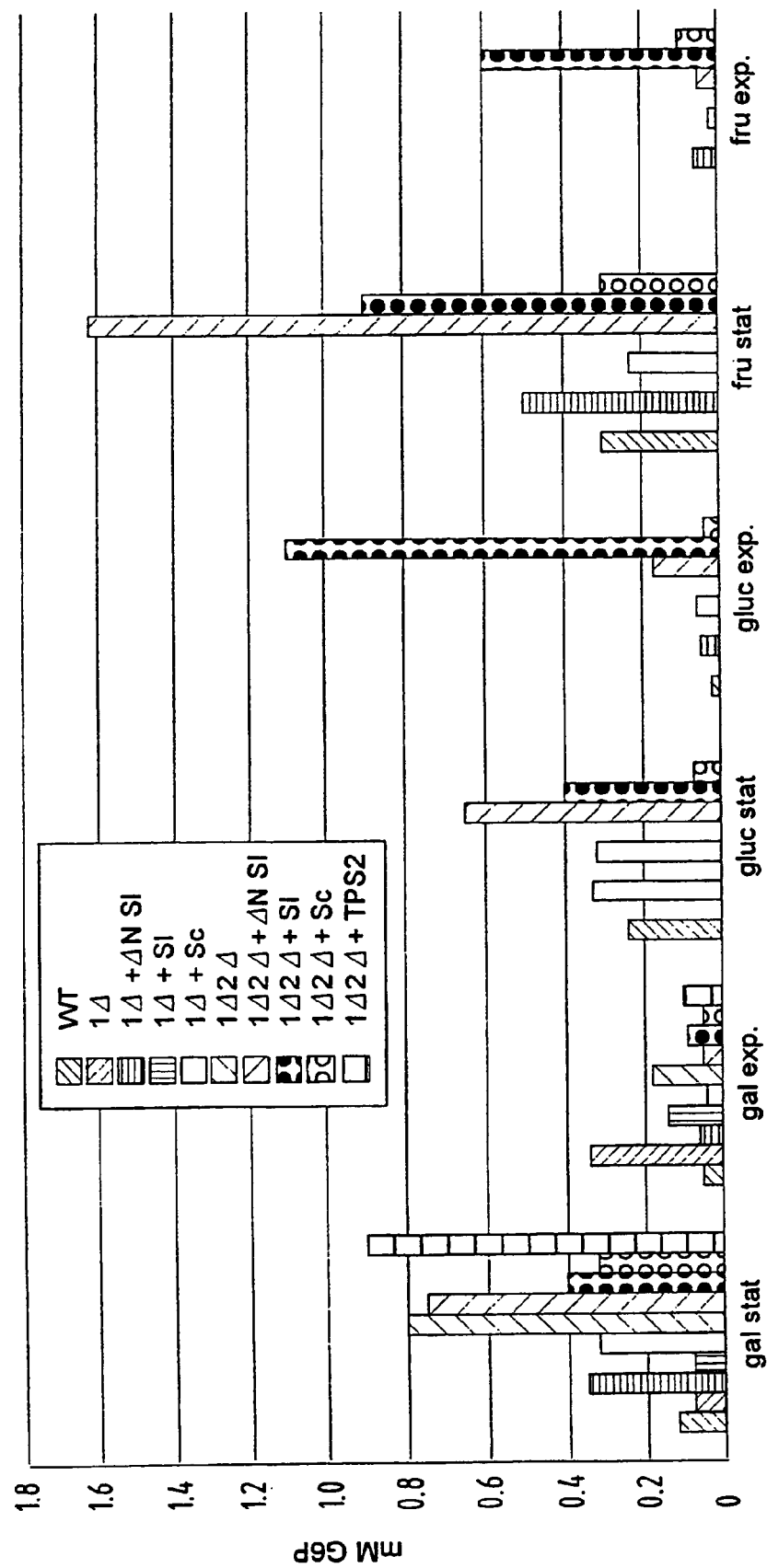
Figure 15E:
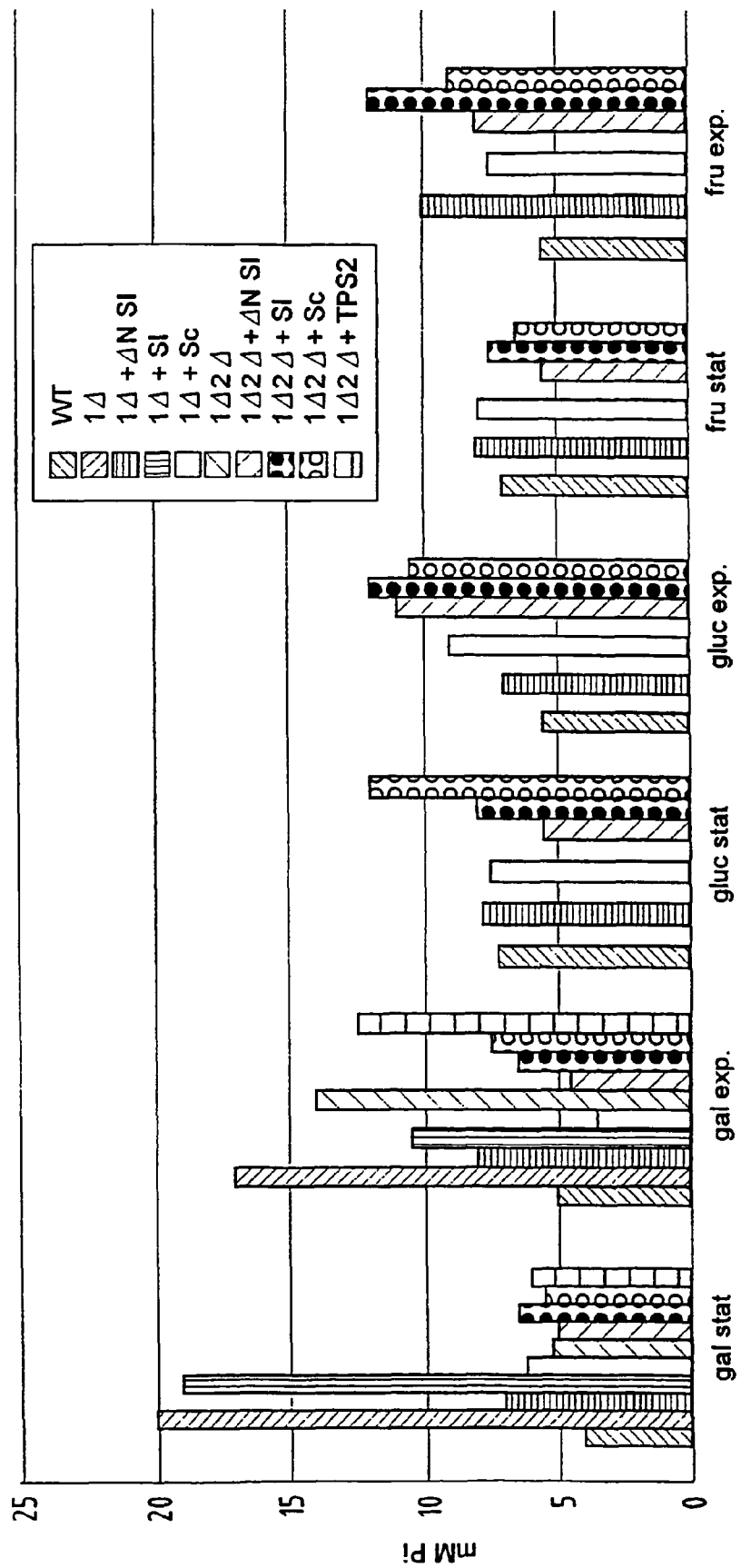
Figure 15F:
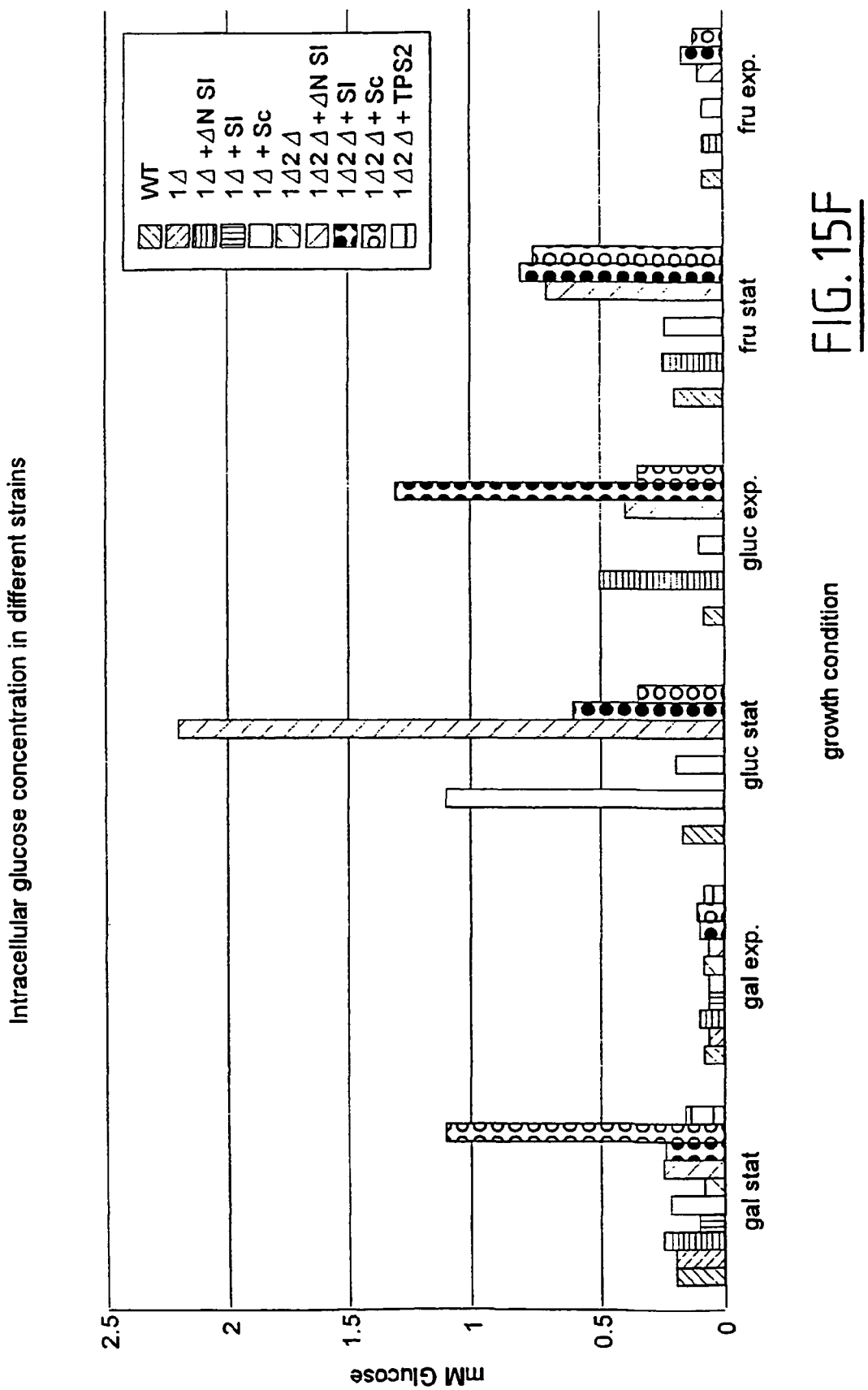

Determination of the glycolytic metabolites was performed on these samples essentially as described by de Koning and van Dam (Anal. Biochem. 204, 118-123, 1992). Using the total amount of protein in the sample as determined according to Lowry et al (J. Biol. Chem. 193, 265-275, 1951), and the assumption of a yeast cytosolic volume of 12 μl per mg protein, cytosolic concentrations were calculated in mM. FIG. 14 shows the result of a representative experiment.

The results clearly indicate that in this short period after the addition of glucose, there is no difference between the metabolite concentrations of the full length and the N-terminal deleted *S. lepidophylla* TPS1 gene. There is a clear hyper accumulation of sugar phosphates after the addition of glucose what is similar to what can be seen for the tps1Δ strain.

These results with the N-terminal deletion constructs show that the accumulation of sugar phosphates is not related to the fact that yeast cells can or cannot grow on glucose. This means that the N-terminal part is important for the control of glucose influx into glycolysis. It also implies that a tps1Δ strain containing the ΔN Sl or ΔN At TPS1 genes can be used as a tool to increase the total flux through glycolysis. This strain grows perfectly on glucose but still a hyper-accumulation of metabolites in the upper part of glycolysis is seen. Overexpression of the enzymes downstream in glycolysis results in a higher flux.

Since the metabolite concentration was only measured over a short period of time after the addition of glucose, another experiment was done where the metabolite concentration was measured during exponential growth and during stationary phase. These results are shown in FIG. 15.

These data confirm the results obtained in the first experiment. There is a hyperaccumulation of sugar phosphates in the tps1Δ strain transformed with the N-terminal deletion construct. From FIGS. 14 and 15 it follows that the difference between the tps1Δ strain and the tps1Δ strain containing the ΔN Sl TPS1 expression plasmid is the ATP level. Whereas the ATP level in the tps1Δ strain drops to zero this is not the case in the other strains. The ATP level that is left is apparently enough to grow on glucose.

The invention claimed is:

1. A method of delaying growth of a plant comprising the steps of:
   a) providing a TPS protein encoded by a plant TPS gene;
   b) designing a suitable modification to the plant TPS gene by truncating or deleting an N-terminal part of the TPS protein encoded by the plant TPS gene in order to achieve an increased trehalose-6-phosphate synthase activity;
   c) cloning the thus modified gene into an expression vector under the control of a constitutive, inducible and/or organ-specific promoter; and
   d) transforming the plant or tissue from the plant with the thus obtained expression vector,
   wherein the growth of the plant is delayed.

2. The method as claimed in claim 1, wherein the TPS gene is the gene from *Selaginella lepidophylla*.

3. The method as claimed in claim 1, wherein the plant TPS gene is from *Arabidopsis thalliana*.

4. The transgenic plant produced by the method of claim 1, having an increased stress tolerance and delayed growth in the whole plant or in specific plant parts.

5. A transgenic plant obtained by the method of claim 1.

6. A transgenic seed from the plant as claimed in claim 4.

7. A transgenic plant obtained from the transgenic seeds as claimed in claim 6.

8. A transgenic progeny from the plants as claimed in claim 4.

9. The method of claim 1, wherein said plant is a crop plant.

10. A method for delaying growth of a plant comprising the steps of:
    e) providing a TPS protein encoded by a plant TPS gene;
    f) designing a suitable modification to the plant TPS gene by deleting or truncating the N-terminal region of the plant TPS gene, which deletion or truncation is of a part of the plant TPS gene that extends beyond the N-terminal region of a yeast TPS gene when aligned to the plant TPS gene, wherein said deletion or truncation achieves an increased trehalose-6-phosphate synthase activity;
    g) cloning the thus modified plant TPS gene into an expression vector under the control of a constitutive, inducible and/or organ-specific promoter; and
    h) transforming the plant or tissue from the plant with the thus obtained expression vector,
    i) wherein the growth of the plant is delayed.

11. The method as claimed in claim 1, wherein the N-terminal part of the TPS protein encoded by the plant TPS gene corresponds to a portion of the plant TPS gene that extends beyond a 5' terminus of a yeast TPS gene.

12. The method as claimed in claim 11, wherein the portion of the plant TPS gene that extends beyond the 5' terminus of the yeast TPS consists essentially of a complete portion of the plant TPS gene that extends beyond the 5' terminus of the yeast TPS gene.

13. The method as claimed in claim 1, wherein the N-terminal part of the TPS protein encoded by the plant TPS gene corresponds to no more than approximately 200 base-pairs from a 5' terminus of the TPS gene.

14. The method as claimed in claim 1, wherein the N-terminal part of the TPS protein encoded by the plant TPS gene corresponds to no more than approximately 300 base-pairs from a 5' terminus of the TPS gene.

15. The method as claimed in claim 1, wherein the plant TPS gene is a *Selaginella* TPS gene or an *Arabidopsis* TPS gene.

16. The method as claimed in claim 1, wherein the plant is selected from the group consisting of *Nicotiana, Solanum, Zea, Oryza, Selaginella*, and *Arabidopsis*.

* * * * *

UNITED STATES PATENT AND TRADEMARK OFFICE
CERTIFICATE OF CORRECTION

| | | Page 1 of 1 |
|---|---|---|
| PATENT NO. | : 7,781,646 B2 | |
| APPLICATION NO. | : 11/065184 | |
| DATED | : August 24, 2010 | |
| INVENTOR(S) | : De La Fuente et al. | |

It is certified that error appears in the above-identified patent and that said Letters Patent is hereby corrected as shown below:

On the Title Page, insert items [63] and [30]:

-- Related U.S. Application Data
(63)  Continuation of application No. 10/110,502, filed on April 15, 2002, now Pat. No. 6,872,870, filed as a 371 of international application No. PCT/EP99/07913, filed on October 15, 1999.

(30)  Foreign Application Priority Data
         Oct. 15, 1998 (EP)................................98203469.6 --

Column 25, lines 9-10, 20, 30-31 and 40, "by DNA" should read -- bp DNA --

Signed and Sealed this
Twenty-eighth Day of December, 2010

David J. Kappos
*Director of the United States Patent and Trademark Office*